US008207342B2

(12) United States Patent
Kühnert et al.

(10) Patent No.: US 8,207,342 B2
(45) Date of Patent: Jun. 26, 2012

(54) SUBSTITUTED 3-AMINO-2-MERCAPTOQUINOLINES AS KCNQ2/3 MODULATORS

(75) Inventors: Sven Kühnert, Düren (DE); Gregor Bahrenberg, Monschau-Konzen (DE); Wolfgang Schröder, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/720,770

(22) Filed: Mar. 10, 2010

(65) Prior Publication Data
US 2010/0234421 A1 Sep. 16, 2010

Related U.S. Application Data

(60) Provisional application No. 61/158,800, filed on Mar. 10, 2009.

(30) Foreign Application Priority Data

Mar. 10, 2009 (EP) .................................... 09003431

(51) Int. Cl.
  *C07D 215/36* (2006.01)
(52) U.S. Cl. ...................................................... 546/157
(58) Field of Classification Search ........................ None
  See application file for complete search history.

(56) References Cited

U.S. PATENT DOCUMENTS

| | | | |
|---|---|---|---|
| 2002/0128277 | A1 | 9/2002 | Dworetzky et al. |
| 2010/0234372 | A1 | 9/2010 | Kuhnert et al. |
| 2010/0234419 | A1 | 9/2010 | Kuhnert et al. |
| 2010/0234428 | A1 | 9/2010 | Kuhnert et al. |
| 2010/0234429 | A1 | 9/2010 | Kuhnert et al. |

FOREIGN PATENT DOCUMENTS

| | | |
|---|---|---|
| DE | 27 06 977 A1 | 8/1978 |
| EP | 0 480 258 A1 | 9/1991 |
| EP | 0 716 077 A1 | 6/1996 |
| EP | 0 900 824 A1 | 3/1999 |
| EP | 1 449 841 A1 | 8/2004 |
| FR | 2 532 939 A1 | 3/1984 |
| WO | 96 26925 A1 | 9/1996 |
| WO | 00 42026 A1 | 7/2000 |
| WO | 01 10380 A2 | 2/2001 |
| WO | 01 10381 A2 | 2/2001 |
| WO | 02 066036 A1 | 8/2002 |
| WO | 2002 074388 A1 | 9/2002 |
| WO | 02 081728 A2 | 10/2002 |
| WO | 2004 026816 A1 | 4/2004 |
| WO | 2004 058704 A2 | 7/2004 |
| WO | 2004 058704 A3 | 7/2004 |
| WO | 2005 035514 A2 | 4/2005 |
| WO | 2005 105733 A1 | 11/2005 |
| WO | 2006 051311 A1 | 5/2006 |
| WO | 2006 092143 A1 | 9/2006 |
| WO | 2006 122799 A1 | 11/2006 |
| WO | 2006 122800 A1 | 11/2006 |
| WO | 2007 015767 A1 | 2/2007 |
| WO | 2007 030582 A2 | 3/2007 |
| WO | 2007 057447 A1 | 5/2007 |
| WO | 2008 011080 A2 | 1/2008 |
| WO | 2008 011110 A2 | 1/2008 |
| WO | 2008 012532 A2 | 1/2008 |
| WO | 2008 046582 A1 | 4/2008 |
| WO | 2009 018466 A1 | 2/2009 |
| WO | 2009 019149 A1 | 2/2009 |
| WO | 2009 052078 A1 | 4/2009 |

OTHER PUBLICATIONS

Martin, Yvonne C. et al., Do Structurally Similar Molecules Have Similar Biological Activity?, 45 J. Med. Chem. 4350-4358, 4536 (2002).*
Hewawasam et al., The Synthesis and Structure-Activity Relationship of 3-amino-4-benzylquinolin-2-ones: Discovery of Novel KCNQ2 Channel Openers, 14 Bioorg. & Med. Chem. Letts. 1615-18 (2004).*
F. Zaragoza Dorwald, Side Reactions in Organic Synthesis; A Guide to Successful Synthesis Design, Wiley-VCH, Weinheim, Preface, p. IX (2005).*
Bennett et al; "A peripheral mononeuropathy in rat that produces disorders of pain sensation like those seen in man" Pain, 33 (1988) 87-107.
Gordon Blackburn-Munro; "The anticonvulsant retigabine attenuates nociceptive behaviours in rat models of persistent and neuropathic pain"; European Journal of Pharmacology 460 (2003) 109-116.
De Sarro et al; "Influence of retigabine on the anticonvulsant activity of some antiepileptic drugs against audiogenic seizures in DBA/2 mice"; Naunyn-Schmiedeberg's Arch Pharmacol (2001) 363: 330-336.
Dencker; "Effect of the new antiepileptic drug retigabine in a rodent model of mania"; ScienceDirect, Epilepsy & Behavior 12 (2008) 49-53.
Dost et al; "The anti-hyperalgesic activity of retigabine is mediated by KCNQ potassium channel activation"; Naunyn-Schmiedeberg's Arch Pharmacol (2004) 369 : 382-390.
Dubuisson et al; "The formalin test: A quantitative study of the analgesic effects of morphine, meperidine, and brain stem stimulation in rats and cats" Pain, 4 (1977) 161-174.
Gribkoff; "The therapeutic potential of neuronal Kv7 (KCNQ) channel modulators: an update"; Expert Opin. Ther. Targets (2008) 12(5): 565-581.
Gribkoff; "The therapeutic potential of neuronal KCNQ channel modulators" Expert Opin. Ther. Targets (2003) 7(6): 737-748.
Hansen et al: "The neuronal KCNQ channel opener retigabine inhibits locomotor activity and reduces forebrain excitatory responses to the psychostimulants cocaine, methylphenidate and phencyclidine"; ScienceDirect, European Journal of Pharmcology 570 (2007) 77-88.
Kim, et al; "An experimental model for peripheral neuropathy produced by segmental spinal nerve ligation in the rat"; Pain, 50 (1992) 355-363.
Korsgaard,et al; "Anxiolytic Effects of Maxipost (BMS-204352) and Retigabine via Activation of Neuronal Kv7 Channels"; The Journal of Pharmacology and Experimental Therapeutics vol. 314, No. 1 :282-292, 2005.

(Continued)

*Primary Examiner* — Janet Andres
*Assistant Examiner* — Timothy R Rozof
(74) *Attorney, Agent, or Firm* — Norris McLaughlin & Marcus, P.A.

(57) ABSTRACT

The invention relates to substituted 3-amino-2-mercaptoquinolines, to processes for their preparation, to medicaments containing these compounds and to the use of these compounds in the preparation of medicaments.

7 Claims, No Drawings

OTHER PUBLICATIONS

Litchfield, Jr. et al; "A simplified method of evaluating dose-effect experiments"; Stamford Research Laboratories, American Cyanamid Company, Stamford, Connecticut, Royal Society of Medicine 1948; pp. 99-113.

Miceli, et al; "Molecular pharmacology and therapeutic potential of neuronal Kv7-modulating drugs"; ScienceDirect, Current Opinion in Pharmacology 2008, 8:65-74.

Nielsen, et al; "Pharmacological characterisation of acid-induced muscle allodynia in rats"; ScienceDirect, European Journal of Pharmacology 487 (2004) 93-103.

Passmore, et al; "KCNQ/M Currents in Sensory Neurons: Significance for Pain Therapy"; The Journal of Neuroscience, Aug. 6, 2003 • 23(18):7227-7236 • 7227.

Richte, et al; "Antidystonic effects of Kv7 (KCNQ) channel openers in the dtsz mutant, an animal model of primary paroxysmal dystonia"; British Journal of Pharmacology (2006) 149, 747-753.

Streng, et al; "Urodynamic effects of the K+ channel (KCNQ) opener retigabine in freely moving, conscious rats"; The Journal of Urology, vol. 172, 2054-2058, Nov. 2004.

Wickenden et al; "KCNQ potassium channels: drug targets for the treatment of epilepsy and pain"; Expert Opinion, Ther. Patents (2004) 14(4): 457-469.

Wermuth, Camille G., "Molecular Variations Based on Isosteric Replacements", The Practice of Medicinal Chemistry, (1996) 203-237.

Yoo et al, "Beckmann rearrangement using indium (III) chloride: synthesis of substituted oxazoloquinolines from the corresponding ketoximes of 3-acyl-1H-quinolin-4-ones"; Synthesis (2006), No. 10, pp. 1599-1612.

CAPLUS 1972:59403.

F. A. Carey, R. J. Sundberg, Advanced Organic Chemistry, Parts A and B, Springer, 5th edition, 2007.

D'Amour and Smith (J. Pharm. Exp. Ther. 72, 74 79 (1941).

J. March, Advanced Organic Chemistry, Wiley & Sons, 6th edition, 2007.

Patani, G. et al, Bioisosterism: a ratiional approach in drug design, Chem. Rev. 1996, pp. 3147-3176.

Silverman, R. The organic chemistry of drug design and drug action, 2004, Elsevier, 2nd edition, p. 9.

* cited by examiner

SUBSTITUTED 3-AMINO-2-MERCAPTOQUINOLINES AS KCNQ2/3 MODULATORS

This application is a non-provisional utility patent application claiming priority of U.S. Provisional Application No. 61/158,800 filed Mar. 10, 2009; and European Patent Application No. 09003431.5 filed Mar. 10, 2009.

The invention relates to substituted 3-amino-2-mercaptoquinolines, to processes for their preparation, to medicaments containing these compounds and to the use of these compounds in the preparation of medicaments.

The treatment of pain, in particular of neuropathic pain, is of great importance in medicine. There is a worldwide need for effective pain therapies. The urgent need for action for a target-orientated treatment of chronic and non-chronic states of pain appropriate for the patient, by which is to be understood the successful and satisfactory treatment of pain for the patient, is also documented in the large number of scientific works which have recently been published in the field of applied analgesics and of fundamental research into nociception.

A pathophysiological feature of chronic pain is the over excitability of neurons. Neuronal excitability is influenced decisively by the activity of $K^+$ channels, since these determine decisively the resting membrane potential of the cell and therefore the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36).

It has accordingly been possible to detect an analgesic activity in preclinical neuropathy and inflammatory pain models for the KCNQ2/3 agonist retigabine (Blackburn-Munro and Jensen, Eur J Pharmacol. 2003; 460(2-3); 109-16; Dost et al., Naunyn Schmiedebergs Arch Pharmacol 2004; 369(4): 382-390).

The KCNQ2/3 $K^+$ channel thus represents a suitable starting point for the treatment of pain; in particular of pain selected from the group consisting of chronic pain, neuropathic pain, inflammatory pain and muscular pain (Nielsen et al., Eur J Pharmacol. 2004; 487(1-3): 93-103), in particular of neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(1-3): 77-88), mania/bipolar disorders (Dencker et al., Epilepsy Behav 2008, 12(1): 49-53), dystonia-associated dyskinesias (Richter et al., Br J Pharmacol 2006, 149(6): 747-53).

Substituted tetrahydropyrrolopyrazines which have an affinity for the KCNQ2/3 $K^+$ channel are known from the prior art (WO 2008/046582).

There is a need for further compounds with comparable or better properties, not only in respect of affinity for KCNQ2/3 as such (potency, efficacy).

For example, it can be advantageous to improve the metabolic stability, the solubility in aqueous media or the permeability of the compounds. These factors can have a positive effect on the oral bioavailability or can change the PK/PD (pharmacokinetic/pharmacodynamic) profile, which can lead, for example, to a more advantageous duration of action.

A weak or non-existent interaction with transporter molecules, which are involved in the uptake and excretion of medicaments, is also to be categorized as an indication of improved bioavailability and low medicament interactions. Further, interactions with the enzymes that are involved in the degradation and excretion of medicaments should also be as low as possible, because such test results likewise indicate that low or no medicament interactions at all are to be expected.

It can also be advantageous for the compounds to exhibit a high selectivity in respect of other receptors of the KCNQ family (specificity), for example in respect of KCNQ1, KCNQ3/5 or KCNQ4. A high selectivity can have a positive effect on the side-effect profile. For example, it is known that compounds which (also) bind to KCNQ1 involve a high risk of cardiac side-effects, for which reason high selectivity in respect of KCNQ1 can be desirable. However, a high selectivity in respect of other receptors can also be advantageous. A low affinity for the hERG ion channel or for the L-type calcium ion channel (phenylalkylamine, benzothiazepine, dihydropyridine binding sites) can be advantageous because those receptors are associated with the occurrence of cardiac side-effects. Overall, an improved selectivity in respect of the binding to other endogenous proteins (i.e. e.g. receptors or enzymes) can lead to an improvement in the side-effect profile and hence to improved tolerability.

An object of the invention was, therefore, to provide novel compounds which have advantages over the compounds of the prior art. The compounds should be suitable in particular as pharmacological active ingredients in medicaments, especially in medicaments for the treatment of disorders or diseases that are mediated at least in part by KCNQ2/3 $K^+$ channels.

That object is achieved by the subject-matter of the patent claims.

It has been found, surprisingly, that substituted 3-amino-2-mercaptoquinolines of the general formula (1) below are suitable for the treatment of pain. It has further been found, surprisingly, that substituted 3-amino-2-mercaptoquinolines of the general formula (1) below also have an excellent affinity for the KCNQ2/3 $K^+$ channel and are therefore suitable for the treatment of disorders or diseases that are mediated at least in part by KCNQ2/3 $K^+$ channels. The substituted 3-amino-2-mercaptoquinolines thereby act as modulators, that is to say agonists or antagonists, of the KCNQ2/3 $K^+$ channel.

The invention provides substituted 3-amino-2-mercaptoquinolines of the general formula (1)

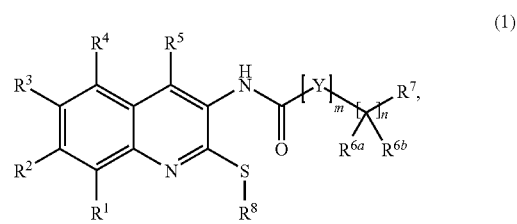

wherein
m represents 0 or 1 and
n represents an integer from 0 to 4, $R^1$, $R^2$, $R^3$, $R^4$, $R^5$, $R^{6a}$, $R^{6b}$ each independently of the others represents H; F; Cl; Br; I; $NO_2$; $CF_3$; CN; OH; $OCF_3$; SH; $SCF_3$; $NH_2$; $C_{1-10}$-alkyl, $O-C_{1-10}$-alkyl, $O-C(=O)-C_{1-10}$-alkyl, $S-C_{1-10}$-alkyl, $NH(C_{1-10}$-alkyl), $N(C_{1-10}$-alkyl)$_2$, $NH-C(=O)-C_{1-10}$-alkyl, $N(C(=O)-C_{1-10}$-alkyl)$_2$ or $C(=O)-C_{1-10}$-alkyl, in each case saturated or unsaturated, branched or unbranched, unsubstituted or mono- or poly-substituted; $C_{3-8}$-cycloalkyl or heterocyclyl, in each case saturated or unsaturated, unsubstituted or mono- or poly-substituted;

Y represents O or $NR^9$,
  wherein $R^9$ represents H or $C_{1-4}$-alkyl, saturated or unsaturated, branched or unbranched, unsubstituted or mono- or poly-substituted;

$R^7$ represents $C_{1-10}$-alkyl or $C_{2-10}$-heteroalkyl, saturated or unsaturated, branched or unbranched, unsubstituted or mono- or poly-substituted; $C_{3-10}$-cycloalkyl or heterocyclyl, in each case saturated or unsaturated, unsubstituted or mono- or poly-substituted; aryl or heteroaryl, in each case unsubstituted or mono- or poly-substituted;
  with the proviso that, when $R^7$ denotes heterocyclyl, the bonding of the heterocyclyl to the general structure of higher order can take place via a carbon atom of the heterocyclyl, preferably the bonding of the heterocyclyl to the general structure of higher order takes place via a carbon atom of the heterocyclyl; and
  with the proviso that, when $R^7$ denotes aryl or heteroaryl, the sum of n and m is greater than or equal to 1;

$R^8$ is selected from the group consisting of $C_{1-10}$-alkyl or $C_{2-10}$-heteroalkyl, in each case saturated or unsaturated, branched or unbranched, unsubstituted or mono- or poly-substituted; $C_{3-10}$-cycloalkyl or heterocyclyl, in each case saturated or unsaturated, unsubstituted or mono- or poly-substituted; aryl or heteroaryl, in each case unsubstituted or mono- or poly-substituted; $C_{1-8}$-alkyl- or $C_{2-8}$-heteroalkyl-bridged $C_{3-10}$-cycloalkyl or heterocyclyl, in each case saturated or unsaturated, unsubstituted or mono- or poly-substituted; or $C_{1-8}$-alkyl- or $C_{2-8}$-heteroalkyl-bridged aryl or heteroaryl, in each case unsubstituted or mono- or poly-substituted, wherein the alkyl or heteroalkyl chain in each case can be branched or unbranched, saturated or unsaturated, unsubstituted;
  wherein "alkyl substituted", "heteroalkyl substituted", "heterocyclyl substituted" and "cycloalkyl substituted" denote the substitution of one or more hydrogen atoms, in each case independently of one another, by F; Cl; Br; I; CN; $CF_3$; =O; =NH; =C($NH_2$)$_2$; $NO_2$; $R^O$; $C(=O)H$; $C(=O)R^O$; $CO_2H$; $C(=O)OR^O$; $CONH_2$; $C(=O)NHR^O$; $C(=O)N(R^O)_2$; OH; $OR^O$; $-O-(C_{1-8}$-alkyl)$-O-$; $O-C(=O)-R^O$; $O-C(=O)-O-R^O$; $O-(C=O)-NH-R^O$; $O-C(=O)-N(R^O)_2$; $O-S(=O)_2-R^O$; $O-S(=O)_2OH$; $O-S(=O)_2OR^O$; $O-S(=O)_2NH_2$; $O-S(=O)_2NHR^O$; $O-S(=O)_2N(R^O)_2$; $NH_2$; $NH-R^O$; $N(R^O)_2$; $NH-C(=O)-R^O$; $NH-C(=O)-O-R^O$; $NH-C(=O)-NH_2$; $NH-C(=O)-NH-R^O$; $NH-C(=O)-N(R^O)_2$; $NR^O-C(=O)-R^O$; $NR^O-C(=O)-O-R^O$; $NR^O-C(=O)-NH_2$; $NR^O-C(=O)-NH-R^O$; $NR^O-C(=O)-N(R^O)_2$; $NH-S(=O)_2OH$; $NH-S(=O)_2R^O$; $NH-S(=O)_2OR^O$; $NH-S(=O)_2NH_2$; $NH-S(=O)_2NHR^O$; $NH-S(=O)_2N(R^O)_2$; $NR^O-S(=O)_2OH$; $NR^O-S(=O)_2R^O$; $NR^O-S(=O)_2OR^O$; $NR^O-S(=O)_2NH_2$; $NR^O-S(=O)_2NHR^O$; $NR^O-S(=O)_2N(R^O)_2$; SH; $SR^O$; $S(=O)R^O$; $S(=O)_2R^O$; $S(=O)_2H$; $S(=O)_2OH$; $S(=O)_2OR^O$; $S(=O)_2NH_2$; $S(=O)_2NHR^O$; $S(=O)_2N(R^O)_2$;
    wherein "aryl substituted" and "heteroaryl substituted" denote the substitution of one or more hydrogen atoms, in each case independently of one another, by F; Cl; Br; I; $NO_2$; $CF_3$; CN; $R^O$; $C(=O)H$; $C(=O)R^O$; $CO_2H$; $C(=O)OR^O$; $CONH_2$; $C(=O)NHR^O$; $C(=O)N(R^O)_2$; OH; $OR^O$; $-O-(C_{1-8}$-alkyl)$-O-$; $O-C(=O)-R^O$; $O-C(=O)-O-R^O$; $O-(C=O)-NH-R^O$; $O-C(=O)-N(R^O)_2$; $O-S(=O)_2-R^O$; $O-S(=O)_2OH$; $O-S(=O)_2OR^O$; $O-S(=O)_2NH_2$; $O-S(=O)_2NHR^O$; $O-S(=O)_2N(R^O)_2$; $NH_2$; $NH-R^O$; $N(R^O)_2$; $NH-C(=O)-R^O$; $NH-C(=O)-O-R^O$; $NH-C(=O)-NH_2$; $NH-C(=O)-NH-R^O$; $NH-C(=O)-N(R^O)_2$; $NR^O-C(=O)-R^O$; $NR^O-C(=O)-O-R^O$; $NR^O-C(=O)-NH_2$; $NR^O-C(=O)-NH-R^O$; $NR^O-C(=O)-N(R^O)_2$; $NH-S(=O)_2OH$; $NH-S(=O)_2R^O$; $NH-S(=O)_2OR^O$; $NH-S(=O)_2NH_2$; $NH-S(=O)_2NHR^O$; $NH-S(=O)_2N(R^O)_2$; $NR^O-S(=O)_2OH$; $NR^O-S(=O)_2R^O$; $NR^O-S(=O)_2OR^O$; $NR^O-S(=O)_2NH_2$; $NR^O-S(=O)_2NHR^O$; $NR^O-S(=O)_2N(R^O)_2$; SH; $SR^O$; $S(=O)R^O$; $S(=O)_2R^O$; $S(=O)_2OH$; $S(=O)_2OR^O$; $S(=O)_2NH_2$; $S(=O)_2NHR^O$; $S(=O)_2N(R^O)_2$; and $R^O$ represents $C_{1-10}$-alkyl or $C_{2-10}$-heteroalkyl, in each case saturated or unsaturated, branched or unbranched, unsubstituted or mono- or poly-substituted; $C_{3-10}$-cycloalkyl or heterocyclyl, in each case saturated or unsaturated, unsubstituted or mono- or poly-substituted; aryl or heteroaryl, in each case unsubstituted or mono- or poly-substituted; $C_{1-8}$-alkyl- or $C_{2-8}$-heteroalkyl-bridged $C_{3-10}$-cycloalkyl or heterocyclyl, in each case saturated or unsaturated, unsubstituted or mono- or poly-substituted, wherein the alkyl or heteroalkyl chain in each case can be branched or unbranched, saturated or unsaturated, unsubstituted, mono- or poly-substituted; or $C_{1-8}$-alkyl- or $C_{2-8}$-heteroalkyl-bridged aryl or heteroaryl, in each case unsubstituted or mono- or poly-substituted, wherein the alkyl or heteroalkyl chain in each case can be branched or unbranched, saturated or unsaturated, unsubstituted, mono- or poly-substituted;

in the form of the free compounds or salts of physiologically acceptable acids or bases.

Within the scope of this invention, the terms "alkyl" or "$C_{1-10}$-alkyl", "$C_{1-8}$-alkyl", "$C_{1-4}$-alkyl" and "$C_{2-10}$-alkyl" include acyclic saturated or unsaturated aliphatic hydrocarbon radicals, which can be branched or unbranched as well as unsubstituted or mono- or poly-substituted, having from 1 to 10 or from 1 to 8 or from 1 to 4 or from 2 to 10 carbon atoms, that is to say $C_{1-10}$-alkanyls, $C_{2-10}$-alkenyls and $C_{2-10}$-alkynyls or $C_{1-8}$-alkanyls, $C_{2-8}$-alkenyls and $C_{2-8}$-alkynyls or $C_{1-4}$-alkanyls, $C_{2-4}$-alkenyls and $C_{2-4}$-alkynyls or $C_{2-10}$-alkanyls, $C_{2-10}$-alkenyls and $C_{2-10}$-alkynyls. Alkenyls contain at least one C—C double bond and alkynyls contain at least one C—C triple bond. Alkyl is preferably selected from the group comprising methyl, ethyl, n-propyl, 2-propyl, n-butyl, isobutyl, sec-butyl, tert-butyl, n-pentyl, isopentyl, neopentyl, n-hexyl, n-heptyl, n-octyl, n-nonyl, n-decyl, ethenyl (vinyl), ethynyl, propenyl ($-CH_2CH=CH_2$, $-CH=CH-CH_3$, $-C(=CH_2)-CH_3$), propynyl ($-CH-C\equiv CH$, $-C\equiv C-CH_3$), butenyl, butynyl, pentenyl, pentynyl, hexenyl and hexynyl, heptenyl, heptynyl, octenyl, octynyl, nonenyl, nonynyl, decenyl and decynyl.

Within the scope of this invention, the terms "heteroalkyl" or "$C_{2-10}$-heteroalkyl", "$C_{2-8}$-heteroalkyl" and "$C_{2-4}$-heteroalkyl" include acyclic aliphatic saturated or unsaturated hydrocarbon radicals having from 2 to 10 carbon atoms, that is to say $C_{2-10}$-heteroalkanyls, $C_{2-10}$-heteroalkenyls and $C_{2-10}$-heteroalkynyls, or having from 2 to 8 carbon atoms, that is to say $C_{2-8}$-heteroalkanyls, $C_{2-8}$-heteroalkenyls and $C_{2-8}$-heteroalkynyls, or having from 2 to 4 carbon atoms, that is to say $C_{2-4}$-heteroalkanyls, $C_{2-4}$-heteroalkenyls and $C_{2-4}$-heteroalkynyls, which in each case can be branched or unbranched as well as unsubstituted or mono- or poly-substituted and in which at least one carbon atom, optionally also two or three carbon atoms, have been replaced by a heteroatom or heteroatom group in each case selected independently of one another from the group consisting of O, S, S(=O), $S(=O)_2$, N, NH and $N(C_{1-8}$-alkyl), preferably $N(CH_3)$, wherein the initial carbon atom of a $C_{2-10}$-heteroalkyl or of a $C_{2-8}$-heteroalkyl or of a $C_{2-4}$-heteroalkyl, via which the $C_{2-10}$- heteroalkyl or $C_{2-8\text{-}heteroalkyl\ or\ C2-4}$-heteroalkyl is bonded to the respective general structure of higher order, cannot be replaced by a heteroatom or heteroatom group and adjacent carbon atoms cannot simultaneously be replaced by a heteroatom or heteroatom group. The heteroatom groups NH and $N(C_{1-8}$-alkyl) of the heteroalkyl can optionally also be mono- or poly-substituted. $C_{2-10}$-Heteroalkenyls, $C_{2-8}$-heteroalkenyls and $C_{2-4}$-heteroalkenyls contain at least one C—C or C—N double bond and $C_{2-10}$-heteroalkynyls, $C_{2-8}$-heteroalkynyls and $C_{2-4}$-heteroalkynyls contain at least one C—C triple bond. Heteroalkyl is preferably selected from the group comprising —CH$_2$—O—CH$_3$, —CH$_2$—CH$_2$—O—CH$_3$, —CH$_2$—CH$_2$—O—CH$_2$—CH$_3$, —CH$_2$—CH$_2$—O—CH$_2$—CH$_2$—O—CH$_3$, —CH═CH—O—CH$_3$, —CH═CH—O—CH$_2$—CH$_3$, ═CH—O—CH$_3$, ═CH—O—CH$_2$—CH$_3$, ═CH—CH$_2$—O—CH$_2$—CH$_3$, ═CH—CH$_2$—O—CH$_3$, —CH$_2$—NH—CH$_3$, —CH$_2$—CH$_2$—NH—CH$_3$, —CH$_2$—CH$_2$—NH—CH$_2$—CH$_3$, —CH$_2$—CH$_2$—NH—CH$_2$—CH$_2$—NH—CH$_3$, —CH═CH—NH—CH$_3$, —CH═CH—NH—CH$_2$—CH$_3$, —CH═CH—N(CH$_3$)—CH$_2$—CH$_3$, ═CH—NH—CH$_3$, ═CH—NH—CH$_2$—CH$_3$, ═CH—CH$_2$—NH—CH$_2$—CH$_3$, ═CH—CH$_2$—NH—CH$_3$, —CH$_2$—N(CH$_3$)—CH$_3$, —CH$_2$—CH$_2$—N(CH$_3$)—CH$_3$, —CH$_2$—CH$_2$—N(CH$_3$)—CH$_2$—CH$_3$, —CH$_2$—CH$_2$—N(CH$_3$)—CH$_2$—CH$_2$—N(CH$_3$)—CH$_3$, CH$_2$—CH$_2$—NH—CH$_2$—CH$_2$—O—CH$_3$, CH$_2$—CH$_2$—O—CH$_2$—CH$_2$—NH—CH$_3$, CH$_2$—CH$_2$—N(CH$_3$)—CH$_2$—CH$_2$—O—CH$_3$, CH$_2$—CH$_2$—O—CH$_2$—CH$_2$—N(CH$_3$)—CH$_3$, CH$_2$—NH—CH$_2$—O—CH$_3$, CH$_2$—O—CH$_2$—NH—CH$_3$, CH$_2$—N(CH$_3$)—CH$_2$—O—CH$_3$, CH$_2$—O—CH$_2$—N(CH$_3$)—CH$_3$, —CH═CH—N(CH$_3$)—CH$_3$, ═CH—N(CH$_3$)—CH$_3$, ═CH—N(CH$_3$)—CH$_2$—CH$_3$, ═CH—CH$_2$—N(CH$_3$)—CH$_2$—CH$_3$, ═CH—CH$_2$—N(CH$_3$)—CH$_3$, —CH$_2$—CH$_2$═N(CH$_3$) and —CH$_2$═N(CH$_3$).

For the purposes of this invention, the term "cycloalkyl" or "$C_{3-10}$-cycloalkyl" denotes cyclic aliphatic hydrocarbons having 3, 4, 5, 6, 7, 8, 9 or 10 carbon atoms, wherein the hydrocarbons can be saturated or unsaturated (but not aromatic), unsubstituted or mono- or poly-substituted. The bonding of the cycloalkyl to the general structure of higher order can take place via any desired and possible ring member of the cycloalkyl radical. The cycloalkyl radicals can also be fused with further saturated, (partially) unsaturated, (hetero)cyclic, aromatic or heteroaromatic ring systems, that is to say with cycloalkyl, heterocyclyl, aryl or heteroaryl, which can themselves be unsubstituted or mono- or poly-substituted. The cycloalkyl radicals can further be bridged one or more times, as, for example, in the case of adamantyl, bicyclo[2.2.1]-heptyl or bicyclo[2.2.2]octyl. Cycloalkyl is preferably selected from the group comprising cyclopropyl, cyclobutyl, cyclopentyl, cyclohexyl, cycloheptyl, cyclooctyl, cyclononyl, cyclodecyl, adamantyl,

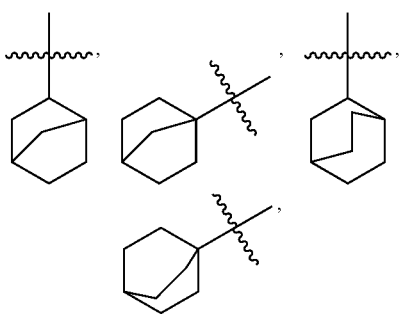

cyclopentenyl, cyclohexenyl, cycloheptenyl and cyclooctenyl.

The term "heterocyclyl" or "heterocycloalkyl" includes aliphatic saturated or unsaturated (but not aromatic) cycloalkyls having from three to ten, that is to say 3, 4, 5, 6, 7, 8, 9 or 10, ring members, in which at least one carbon atom, optionally also two or three carbon atoms, has been replaced by a heteroatom or heteroatom group in each case selected independently of one another from the group consisting of O, S, N, NH and $N(C_{1-8}$-alkyl), preferably $N(CH_3)$, wherein the ring members can be unsubstituted or mono- or poly-substituted. The bonding of the heterocyclyl to the general structure of higher order can take place via any desired and possible ring member of the heterocyclyl radical. The heterocyclyl radicals can also be fused with further saturated, (partially) unsaturated (hetero)cyclic or aromatic or heteroaromatic ring systems, that is to say with cycloalkyl, heterocyclyl, aryl or heteroaryl, which can themselves be unsubstituted or mono- or poly-substituted. Heterocyclyl radicals are preferably selected from the group comprising azetidinyl, aziridinyl, azepanyl, azocanyl, diazepanyl, dithiolanyl, dihydroquinolinyl, dihydropyrrolyl, dioxanyl, dioxolanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl.

Within the scope of this invention, the term "aryl" denotes aromatic hydrocarbons having up to 14 ring members, inter alia phenyls and naphthyls. Each aryl radical can be unsubstituted or mono- or poly-substituted, it being possible for the aryl substituents to be identical or different and to be in any desired and possible position of the aryl. The aryl can be bonded to the general structure of higher order via any desired and possible ring member of the aryl radical. The aryl radicals can also be fused with further saturated, (partially) unsaturated, (hetero)cyclic, aromatic or heteroaromatic ring systems, that is to say with cycloalkyl, heterocyclyl, aryl or heteroaryl, which can themselves be unsubstituted or mono- or poly-substituted. Preferred fused aryl radicals are benzodioxolanyl and benzodioxanyl. Aryl is preferably selected from the group containing phenyl, 1-naphthyl and 2-naphthyl, each of which can be unsubstituted or mono- or poly-substituted. A particularly preferred aryl is phenyl, unsubstituted or mono- or poly-substituted.

The term "heteroaryl" represents a 5- or 6-membered cyclic aromatic radical which contains at least 1 heteroatom, optionally also 2, 3, 4 or 5 heteroatoms, wherein the heteroatoms are in each case selected independently of one another from the group S, N and O and the heteroaryl radical can be unsubstituted or mono- or poly-substituted; in the case of substitution on the heteroaryl, the substituents can be identical or different and can be in any desired and possible position of the heteroaryl. Bonding to the general structure of higher order can take place via any desired and possible ring member of the heteroaryl radical. The heteroaryl can also be part of a bi- or poly-cyclic system having up to 14 ring members, wherein the ring system can be formed with further saturated, (partially) unsaturated, (hetero)cyclic or aromatic or heteroaromatic rings, that is to say with cycloalkyl, heterocyclyl, aryl or heteroaryl, which can themselves be unsubstituted or mono- or poly-substituted. It is preferred for the heteroaryl radical to be selected from the group comprising benzofuranyl, benzimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazolyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. Furyl, pyridyl and thienyl are particularly preferred.

Within the scope of the invention, the expressions "$C_{1-4}$-alkyl- or $C_{1-8}$-alkyl-bridged aryl, heteroaryl, heterocyclyl or cycloalkyl" mean that $C_{1-4}$-alkyl or $C_{1-8}$-alkyl and aryl or heteroaryl or heterocyclyl or cycloalkyl have the meanings defined above and the aryl or heteroaryl or heterocyclyl or cycloalkyl radical is bonded to the general structure of higher order via a $C_{1-4}$-alkyl or $C_{1-8}$-alkyl group. The alkyl chain can in all cases be saturated or unsaturated, branched or unbranched, unsubstituted or mono- or poly-substituted. $C_{1-4}$-Alkyl or $C_{1-8}$-alkyl is preferably selected from the group comprising —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$—, —CH$_2$—(CH$_2$)$_4$—CH$_2$—, —CH═CH—, —CH═CH—CH$_2$—, —C(CH$_3$)═CH$_2$—, —CH═CH—CH$_2$—CH$_2$—, —CH$_2$—CH═CH—CH$_2$—, —CH═CH—CH═CH—, —C(CH$_3$)═CH—CH$_2$—, —CH═C(CH$_3$)—CH$_2$—, —C(CH$_3$)═C(CH$_3$)—, —C(CH$_2$CH$_3$)═CH—, —CH═CH—CH$_2$—CH$_2$—CH$_2$—, —CH$_2$—CH═CH—CH$_2$—CH$_2$—, —CH═CH—CH—CH$_2$—CH$_2$—, —CH═CH$_2$—CH—CH═CH$_2$—, —C≡C—, —C≡C—CH$_2$—, —C≡O—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

Within the scope of the invention, the expressions "$C_{2-8}$-heteroalkyl-bridged aryl, heteroaryl, heterocyclyl or cycloalkyl" and "$C_{2-4}$-heteroalkyl-bridged aryl, heteroaryl, heterocyclyl or cycloalkyl" mean that $C_{2-8}$-heteroalkyl or $C_{2-4}$-heteroalkyl and aryl or heteroaryl or heterocyclyl or cycloalkyl have the meanings defined above and the aryl or heteroaryl or heterocyclyl or cycloalkyl radical is bonded to the general structure of higher order via a $C_{2-8}$-heteroalkyl group or $C_{2-4}$-heteroalkyl group. The heteroalkyl chain can in all cases be saturated or unsaturated, branched or unbranched, unsubstituted or mono- or poly-substituted. If a terminal carbon atom of the $C_{2-8}$-heteroalkyl group or $C_{2-4}$-heteroalkyl group has been replaced by a heteroatom or heteroatom group, then the bonding of a heteroaryl or heterocyclyl to the heteroatom or heteroatom group of the $C_{2-8}$-heteroalkyl or $C_{2-4}$-heteroalkyl always takes place via a carbon atom of the heteroaryl or heterocyclyl. The terminal carbon atom is understood as being the carbon atom within the $C_{2-8}$-heteroalkyl or $C_{2-4}$-heteroalkyl that is furthest in the chain from the general structure of higher order. If the terminal carbon atom of a $C_{2-8}$-heteroalkyl has been replaced, for example, by an N(CH$_3$) group, that group is located within the $C_{2-8}$-heteroalkyl furthest from the general structure of higher order and is bonded to the aryl or heteroaryl or heterocyclyl or cycloalkyl radical. $C_{2-8}$-Heteroalkyl or $C_{2-4}$-heteroalkyl is preferably selected from the group comprising —CH$_2$—NH—, —CH$_2$—N(CH$_3$)—, —CH$_2$—O—, —CH$_2$—CH$_2$—NH—, —CH$_2$—CH$_2$—N(CH$_3$)—, —CH$_2$—CH$_2$—O—, —CH$_2$—CH$_2$—CH$_2$—NH—, —CH$_2$—CH$_2$—CH$_2$—N(CH$_3$)—, —CH$_2$—CH$_2$—CH$_2$—O—, —CH$_2$—O—CH$_2$—, —CH$_2$—CH$_2$—O—CH$_2$—, —CH$_2$—CH$_2$—O—CH$_2$—CH$_2$—, —CH$_2$—CH$_2$—O—CH$_2$—CH$_2$—O—CH$_2$—, —CH═CH—O—CH$_2$—, —CH═CH—O—CH$_2$—CH$_2$—, ═CH—O—CH$_2$—, ═CH—O—CH$_2$—CH$_2$—, ═CH—CH$_2$—O—CH$_2$—CH$_2$—, ═CH—CH$_2$—O—CH$_2$—, —CH$_2$—NH—CH$_2$—, —CH$_2$—CH$_2$—NH—CH$_2$—, —CH$_2$—CH$_2$—NH—CH$_2$—CH$_2$—, —CH$_2$—CH$_2$—NH—CH$_2$—CH$_2$—NH—CH$_2$, —CH═CH—NH—CH$_2$—, —CH═CH—NH—CH$_2$—CH$_2$—, —CH═CH—N(CH$_3$)—CH$_2$—CH$_2$—, ═CH—NH—CH$_2$—, ═CH—NH—CH$_2$—CH$_2$—, ═CH—CH$_2$—NH—CH$_2$—CH$_2$—, ═CH—CH$_2$—NH—CH$_2$—, —CH$_2$—N(CH$_3$)—CH$_2$—, —CH$_2$—CH$_2$—N(CH$_3$)—CH$_2$—, —CH$_2$—CH$_2$—N(CH$_3$)—, —CH$_2$—CH$_2$—N(CH$_3$)—CH$_2$—CH$_2$—, —CH$_2$—N(CH$_3$)—CH$_2$—, —CH$_2$—CH$_2$—NH—CH$_2$—CH$_2$—O—CH$_2$—, —CH$_2$—CH$_2$—O—CH$_2$—CH$_2$—NH—CH$_2$—, —CH$_2$—CH$_2$—N(CH$_3$)—CH$_2$—CH$_2$—O—CH$_2$—, —CH$_2$—CH$_2$—O—CH$_2$—CH$_2$—N(CH$_3$)—CH$_2$—, —CH$_2$—NH—CH$_2$—O—CH$_2$—, —CH$_2$—O—CH$_2$—NH—CH$_2$—, —CH$_2$—N(CH$_3$)—CH$_2$—O—CH$_2$—, —CH$_2$—O—CH$_2$—N(CH$_3$)—CH$_2$—, —CH═CH—N(CH$_3$)—CH$_2$—, ═CH—N(CH$_3$)—CH$_2$—, ═CH—N(CH$_3$)—CH$_2$—CH$_2$—, ═CH—CH$_2$—N(CH$_3$)—CH$_2$—CH$_2$—, ═CH—CH$_2$—N(CH$_3$)—CH$_2$—, —CH$_2$—S—, —CH$_2$—CH$_2$—S—, —CH$_2$—CH$_2$—CH$_2$—S—, —CH$_2$—CH$_2$—CH$_2$—S—, —CH$_2$—CH$_2$—S(═O)$_2$—, —CH$_2$—CH$_2$—S(═O)$_2$—, —CH$_2$—CH$_2$—CH$_2$—S(═O)$_2$— and —CH$_2$—CH$_2$—CH$_2$—CH$_2$—S(═O)$_2$—.

In connection with "alkyl", "heteroalkyl", "heterocyclyl" and "cycloalkyl", the expression "mono- or poly-substituted" is understood as meaning within the scope of this invention the substitution of one or more hydrogen atoms one or more times, for example two, three or four times, in each case independently of one another, by substituents selected from the group comprising F; Cl; Br; I; CN; CF$_3$; ═O; ═NH; ═C(NH$_2$)$_2$; NO$_2$; R$^0$; C(═O)H; C(═O)R$^0$; CO$_2$H; C(═O)OR$^0$; CONH$_2$; C(═O)NHR$^0$; C(═O)N(R$^0$)$_2$; OH; OR$^0$; —O—(C$_{1-8}$-alkyl)—O—; O—C(═O)—R$^0$; O—C(═O)—O—R$^0$; O—(C═O)—NH—R$^0$; O—C(═O)—N(R$^0$)$_2$; O—S(═O)$_2$—R$^0$; O—S(═O)$_2$OH; O—S(═O)$_2$OR$^0$; O—S(═O)$_2$NH$_2$; O—S(═O)$_2$NHR$^0$; O—S(═O)$_2$N(R$^0$)$_2$; NH$_2$; NH—R$^0$; N(R$^0$)$_2$; NH—C(═O)—R$^0$; NH—C(═O)—O—R$^0$; NH—C(═O)—NH$_2$; NH—C(═O)—NH—R$^0$; NH—C(═O)—N(R$^0$)$_2$; NR$^0$—C(═O)—R$^0$; NR$^0$—C(═O)—O—R$^0$; NR$^0$—C(═O)—NH$_2$; NR$^0$—C(═O)—NH—R$^0$; NR$^0$—C(═O)—N(R$^0$)$_2$; NH—S(═O)$_2$OH; NH—S(═O)$_2$R$^0$; NH—S(═O)$_2$OR$^0$; NH—S(═O)$_2$NH$_2$; NH—S(═O)$_2$NHR$^0$; NH—S(═O)$_2$N(R$^0$)$_2$; NR$^0$—S(═O)$_2$OH; NR$^0$—S(═O)$_2$R$^0$; NR$^0$—S(═O)$_2$OR$^0$; NR$^0$—S(═O)$_2$NH$_2$; NR$^0$—S(═O)$_2$NHR$^0$; NR$^0$—S(═O)$_2$N(R$^0$)$_2$; SH; SR$^0$; S(═O)R$^0$; S(═O)$_2$R$^0$; S(═O)$_2$OH; S(═O)$_2$OR$^0$; S(═O)$_2$NH$_2$; S(═O)$_2$NHR$^0$; S(═O)$_2$N(R$^0$)$_2$, wherein polysubstituted radicals are to be understood as being radicals that are substituted several times, for example two, three or four times, either on different atoms or on the same atom, for example three times on the same carbon atom, as in the case of $CF_3$ or $CH_2CF_3$, or at different places, as in the case of $CH(OH)-CH=CH-CHCl_2$. A substituent can itself optionally be mono- or poly-substituted. Polysubstitution can take place with the same or with different substituents.

Preferred "alkyl", "heteroalkyl", "heterocyclyl" and "cycloalkyl" substituents are selected from the group comprising F; Cl; Br; I; $NO_2$; $CF_3$; CN; =O; =NH; $R^o$; C(=O)($R^o$ or H); C(=O)O($R^o$ or H); C(=O)N($R^o$ or H)$_2$; OH; $OR^o$; O—C(=O)—$R^o$; O—($C_{1-8}$-alkyl)—OH; —O—($C_{1-8}$-alkyl)—O—; O—($C_{1-8}$-alkyl)—O—$C_{1-8}$-alkyl; $OCF_3$; N($R^o$ or H)$_2$; N($R^o$ or H)—C(=O)—$R^o$; N($R^o$ or H)—C(=O)—N($R^o$ or H)$_2$; SH; $SCF_3$; $SR^o$; S(=O)$_2R^o$; S(=O)$_2$O($R^o$ or H) and S(=O)$_2$—N($R^o$ or H)$_2$.

Particularly preferred "alkyl", "heteroalkyl", "heterocyclyl" and "cycloalkyl" substituents are selected from the group consisting of F; Cl; Br; I; $NO_2$; $CF_3$; CN; =O; $C_{1-8}$-alkyl; aryl; heteroaryl; $C_{3-10}$-cycloalkyl; heterocyclyl; $C_{1-8}$-alkyl-bridged aryl, heteroaryl, $C_{3-10}$-cycloalkyl or heterocyclyl; CHO; C(=O)$C_{1-8}$-alkyl; C(=O)aryl; C(=O)heteroaryl; $CO_2$H; C(=O)O—$C_{1-8}$-alkyl; C(=O)O-aryl; C(=O)O-heteroaryl; $CONH_2$; C(=O)NH—$C_{1-8}$-alkyl; C(=O)N($C_{1-8}$-alkyl)$_2$; C(=O)NH-aryl; C(=O)N(aryl)$_2$; C(=O)NH-heteroaryl; C(=O)N(heteroaryl)$_2$; C(=O)N($C_{1-8}$-alkyl)(aryl); C(=O)N($C_{1-8}$-alkyl)(heteroaryl); C(=O)N(heteroaryl)(aryl); OH; O—$C_{1-8}$-alkyl; $OCF_3$; —O—($C_{1-8}$-alkyl)—O—; O—($C_{1-8}$-alkyl)—OH; O—($C_{1-8}$-alkyl)—O—$C_{1-8}$-alkyl; O-benzyl; O-aryl; O-heteroaryl; O—C(=O)$C_{1-8}$-alkyl; O—C(=O)aryl; O—C(=O)heteroaryl; $NH_2$, NH—$C_{1-8}$-alkyl; N($C_{1-8}$-alkyl)$_2$; NH—C(=O)$C_{1-8}$-alkyl; NH—C(=O)-aryl; NH—C(=O)-heteroaryl; SH; S—$C_{1-8}$-alkyl; $SCF_3$; S-benzyl; S-aryl; S-heteroaryl; S(=O)$_2C_{1-8}$-alkyl; S(=O)$_2$aryl; S(=O)$_2$heteroaryl; S(=O)$_2$OH; S(=O)$_2$O—$C_{1-8}$-alkyl; S(=O)$_2$O-aryl; S(=O)$_2$O-heteroaryl; S(=O)$_2$—NH—$C_{1-8}$-alkyl; S(=O)$_2$—NH-aryl; and S(=O)$_2$—NH—$C_{1-8}$-heteroaryl.

In connection with "aryl" and "heteroaryl", "mono- or poly-substituted" is understood within the scope of this invention as meaning the substitution of one or more hydrogen atoms of the ring system one or more times, for example two, three or four times, in each case independently of one another, by substituents selected from the group comprising F; Cl; Br; I; $NO_2$; $CF_3$; CN; $R^o$; C(=O)H; C(=O)$R^o$; $CO_2$H; C(=O)$OR^o$; $CONH_2$; C(=O)$NHR^o$; C(=O)N($R^o$)$_2$; OH; $OR^o$; —O—($C_{1-8}$-alkyl)—O—; O—C(=O)—$R^o$; O—C(=O)—O—$R^o$; O—(C=O)—NH—$R^o$; O—C(=O)—N($R^o$)$_2$; O—S(=O)$_2$—$R^o$; O—S(=O)$_2$OH; O—S(=O)$_2$$OR^o$; O—S(=O)$_2NH_2$; O—S(=O)$_2NHR^o$; O—S(=O)$_2$N($R^o$)$_2$; $NH_2$; NH—$R^o$; N($R^o$)$_2$; NH—C(=O)—$R^o$; NH—C(=O)—O—$R^o$; NH—C(=O)—$NH_2$; NH—C(=O)—NH—$R^o$; NH—C(=O)—N($R^o$)$_2$; $NR^o$—C(=O)—$R^o$; $NR^o$—C(=O)—O—$R^o$; $NR^o$—C(=O)—$NH_2$; $NR^o$—C(=O)—NH—$R^o$; $NR^o$—C(=O)—N($R^o$)$_2$; NH—S(=O)$_2$OH; NH—S(=O)$_2R^o$; NH—S(=O)$_2$$OR^o$; NH—S(=O)$_2NH_2$; NH—S(=O)$_2NHR^o$; NH—S(=O)$_2$N($R^o$)$_2$; $NR^o$—S(=O)$_2$OH; $NR^o$—S(=O)$_2R^o$; $NR^o$—S(=O)$_2OR^o$; $NR^o$—S(=O)$_2NH_2$; $NR^o$—S(=O)$_2NHR^o$; $NR^o$—S(=O)$_2$N($R^o$)$_2$; SH; $SR^o$; S(=O)$R^o$; S(=O)$_2R^o$; S(=O)$_2$OH; S(=O)$_2OR^o$; S(=O)$_2NH_2$; S(=O)$_2NHR^o$; S(=O)$_2$N($R^o$)$_2$, on one atom or optionally on different atoms, wherein a substituent can itself optionally be mono- or poly-substituted. Polysubstitution is carried out with the same or with different substituents.

Preferred "aryl" and "heteroaryl" substituents are F; Cl; Br; I; $NO_2$; $CF_3$; CN; $R^o$; C(=O)($R^o$ or H); C(=O)O($R^o$ or H); C(=O)N($R^o$ or H)$_2$; OH; $OR^o$; O—C(=O)—$R^o$; —O—($C_{1-8}$-alkyl)—O—; O—($C_{1-8}$-alkyl)—O—$C_{1-8}$-alkyl; $OCF_3$; N($R^o$ or H)$_2$; N($R^o$ or H)—C(=O)—$R^o$; N($R^o$ or H)—C(=O)—N($R^o$ or H)$_2$; SH; $SCF_3$; $SR^o$; S(=O)$_2R^o$; S(=O)$_2$O($R^o$ or H); S(=O)$_2$—N($R^o$ or H)$_2$.

Particularly preferred "aryl" and "heteroaryl" substituents are selected from the group consisting of F; Cl; Br; I; $NO_2$; $CF_3$; CN; $C_{1-8}$-alkyl; aryl; heteroaryl; $C_{3-10}$-cycloalkyl; heterocyclyl; $C_{1-8}$-alkyl-bridged aryl, heteroaryl, $C_{3-10}$-cycloalkyl or heterocyclyl; CHO; C(=O)$C_{1-8}$-alkyl; C(=O)aryl; C(=O)heteroaryl; $CO_2$H; C(=O)O—$C_{1-8}$-alkyl; C(=O)O-aryl; C(=O)O-heteroaryl; $CONH_2$; C(=O)NH—$C_{1-8}$-alkyl; C(=O)N($C_{1-8}$-alkyl)$_2$; C(=O)NH-aryl; C(=O)N(aryl)$_2$; C(=O)NH-heteroaryl; C(=O)N(heteroaryl)$_2$; C(=O)N($C_{1-8}$-alkyl)(aryl); C(=O)N($C_{1-8}$-alkyl)(heteroaryl); C(=O)N(heteroaryl)(aryl); OH; O—$C_{1-8}$-alkyl; $OCF_3$; —O—($C_{1-8}$-alkyl)—O—; O—($C_{1-8}$-alkyl)—OH; O—($C_{1-8}$-alkyl)—O—$C_{1-8}$-alkyl; O-benzyl; O-aryl; O-heteroaryl; O—C(=O)$C_{1-8}$-alkyl; O—C(=O)aryl; O—C(=O)heteroaryl; $NH_2$; NH—$C_{1-8}$-alkyl; N($C_{1-8}$-alkyl)$_2$; NH—C(=O)$C_{1-8}$-alkyl; NH—C(=O)-aryl; NH—C(=O)-heteroaryl; SH; S—$C_{1-8}$-alkyl; $SCF_3$; S-benzyl; S-aryl; S-heteroaryl; S(=O)$_2C_{1-8}$-alkyl; S(=O)$_2$aryl; S(=O)$_2$heteroaryl; S(=O)$_2$OH; S(=O)$_2$O—$C_{1-8}$-alkyl; S(=O)$_2$O-aryl; S(=O)$_2$O-heteroaryl; S(=O)$_2$—NH—$C_{1-8}$-alkyl; S(=O)$_2$—NH-aryl; S(=O)$_2$—NH—$C_{1-8}$-heteroaryl.

The compounds according to the invention are defined by substituents, for example by $R^1$, $R^2$ and $R^3$ (1st generation substituents), which are themselves optionally substituted (2nd generation substituents). Depending on the definition, these substituents of the substituents can in turn themselves be substituted (3rd generation substituents). If, for example, $R^3=R^o$, wherein $R^o$=aryl (1st generation substituent), aryl can itself be substituted, for example by $NHR^o$, wherein $R^o=C_{1-10}$-alkyl (2nd generation substituent). This yields the functional group aryl-$NHC_{1-10}$-alkyl. $C_{1-10}$-Alkyl can then in turn itself be substituted, for example by Cl (3rd generation substituent). Overall, this then yields the functional group aryl-$NHC_{1-10}$-alkyl-Cl.

In a preferred embodiment, however, the 3rd generation substituents cannot themselves be substituted, that is to say there are no 4th generation substituents. In another preferred embodiment, the 2nd generation substituents cannot themselves be substituted, that is to say there are not even any 3rd generation substituents. In other words, the functional groups for $R^o$ to $R^8$ in each case can optionally be substituted in this embodiment, for example in the case of the general formula (1), but the substituents cannot themselves be substituted.

In some cases, the compounds according to the invention are defined by substituents which are or carry an aryl or heteroaryl radical, in each case unsubstituted or mono- or poly-substituted, or which, together with the carbon atom(s) or heteroatom(s) joining them as ring member(s), form a ring, for example an aryl or heteroaryl, in each case unsubstituted or mono- or poly-substituted. Both these aryl or heteroaryl radicals and the aromatic ring systems so formed can optionally be fused with $C_{3-10}$-cycloalkyl or heterocyclyl, in each case saturated or unsaturated, that is to say with a $C_{3-10}$-cycloalkyl such as cyclopentyl or with a heterocyclyl such as morpholinyl, it being possible for the $C_{3-10}$-cycloalkyl or heterocyclyl radicals so fused to be unsubstituted or mono- or poly-substituted.

In some cases, the compounds according to the invention are defined by substituents which are or carry a $C_{3-10}$-cycloalkyl or heterocyclyl radical, in each case unsubstituted or mono- or poly-substituted, or which, together with the carbon atom(s) or heteroatom(s) joining them as ring member(s), form a ring, for example a $C_{3-10}$-cycloalkyl or heterocyclyl, in each case unsubstituted or mono- or poly-substituted. Both these $C_{3-10}$-cycloalkyl or heterocyclyl radicals and the aliphatic ring systems formed can optionally be fused with aryl or heteroaryl, that is to say with an aryl such as phenyl or with a heteroaryl such as pyridyl, it being possible for the aryl or heteroaryl radicals so fused to be unsubstituted or mono- or poly-substituted. The ring systems so formed are preferably fused with an aryl, particularly preferably with phenyl. If the substituents $R^9$ and $R^{10}$ form, for example, with the nitrogen atom joining them, a piperidinyl, then the piperidinyl ring can be fused with phenyl to form tetrahydroisoquinolinyl.

Within the scope of the present invention, the symbol

used in formulae denotes a linking of a corresponding radical to the general structure of higher order.

The expression "salt formed with a physiologically acceptable acid" is understood within the scope of this invention as meaning salts of the active ingredient in question with inorganic or organic acids that are physiologically acceptable—in particular when used in humans and/or mammals. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, saccharinic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. Citric acid and hydrochloric acid are particularly preferred.

Physiologically acceptable salts with cations or bases are salts of the compound in question—in the form of the anion with at least one, preferably inorganic cation—that are physiologically acceptable—in particular when used in humans and/or mammals. Particular preference is given to the salts of the alkali and alkaline earth metals but also to ammonium salts, but in particular to (mono-) or (di-)sodium, (mono-) or (di-)potassium, magnesium or calcium salts.

In a preferred embodiment of the invention, m represents 0.

In an embodiment of the invention that is likewise preferred, n represents 1, 2 or 3.

In a further preferred embodiment, the substituents $R^1$, $R^2$, $R^3$, $R^4$ and $R^5$ each independently of the others are selected from the group consisting of H; F; Cl; Br; I; $NO_2$; $CF_3$; CN; OH; $OCF_3$; SH; $SCF_3$; $NH_2$; $C_{1-8}$-alkyl, O—$C_{1-8}$-alkyl, O—C(=O)—$C_{1-8}$-alkyl, S—$C_{1-8}$-alkyl, NH($C_{1-8}$-alkyl), N($C_{1-8}$-alkyl)$_2$, NH—C(=O)—$C_{1-8}$-alkyl, N(C(=O)—$C_{1-8}$-alkyl)$_2$ or C(=O)—$C_{1-8}$-alkyl, in each case saturated or unsaturated, branched or unbranched, unsubstituted or mono- or poly-substituted; $C_{3-7}$-cycloalkyl or heterocyclyl, in each case saturated or unsaturated, unsubstituted or mono- or poly-substituted.

Preferably, $R^1$, $R^2$, $R^3$, $R^4$ and $R^5$ each independently of the others are selected from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl, in each case saturated or unsaturated, branched or unbranched, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{3-6}$-cycloalkyl or heterocyclyl, in each case saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl.

Particularly preferably, $R^1$, $R^2$, $R^3$ and $R^4$ each independently of the others represents H; F; Cl; CN; $OCF_3$; $SCF_3$; $CF_3$; $CH_3$ or $OCH_3$;

and $R^5$ denotes H, F, Cl, $OCF_3$, $SCF_3$, $C_{1-6}$-alkyl, O—$C_{1-6}$-alkyl, S—$C_{1-6}$-alkyl, in particular H, $C_{1-4}$-alkyl, O—$C_{1-4}$-alkyl, most particularly preferably H, $CH_3$, $OCH_3$.

Preferably, $R^{6a}$ and $R^{6b}$ each independently of the other denote H; F; Cl; Br; I; methyl; ethyl; n-propyl; isopropyl; n-butyl; sec-butyl; tert-butyl; OH; O-methyl or O-ethyl, particularly preferably H, $CH_3$ or $OCH_3$.

Preferably, $R^7$ denotes $C_{1-8}$-alkyl or $C_{2-8}$-heteroalkyl, saturated or unsaturated; branched or unbranched, unsubstituted or mono- or poly-substituted by one ore more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{3-8}$-cycloalkyl or heterocyclyl, saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; aryl or heteroaryl, in each case unsubstituted or mono- or poly-substituted by one or more substituents selected independently of one another from the group consisting of H; F; Cl; Br; I; $NO_2$; $CF_3$; CN; $NO_2$; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl.

Particularly preferably, $R^7$ represents $C_{2-6}$-alkyl or $C_{2-6}$-heteroalkyl, saturated or unsaturated; branched or unbranched, unsubstituted; $C_3$-cycloalkyl or heterocyclyl, saturated or unsaturated, unsubstituted; phenyl, furyl, thienyl or pyridyl, in each case unsubstituted or mono- or poly-substituted by one or more substituents selected independently of one another from the group consisting of F, Cl, Br, I, CN; $CF_3$, $OCF_3$, $SCF_3$, $CH_3$ and $OCH_3$.

In a preferred embodiment of the invention, m represents 0, n represents 1, 2 or 3 and $R^7$ represents aryl or heteroaryl, in each case unsubstituted or mono- or poly-substituted.

In a particularly preferred embodiment of the invention, m represents 0, n represents 1 and $R^7$ represents aryl or heteroaryl, in each case unsubstituted or mono- or poly-substituted.

In a most particularly preferred embodiment of the invention, m represents 0, n represents 1 and $R^7$ represents phenyl, thienyl or pyridyl, in each case unsubstituted or mono- or poly-substituted by one or more substituents selected independently of one another from the group consisting of F, Cl, Br, I, CN, $CF_3$, $OCF_3$, $SCF_3$, $CH_3$ and $OCH_3$.

In another preferred embodiment of the invention, m represents 0, n represents 1 or 2 and $R^7$ represents $C_{1-10}$-alkyl or $C_{2-10}$-heteroalkyl, saturated or unsaturated; branched or unbranched, unsubstituted or mono- or poly-substituted; $C_{3-10}$-cycloalkyl or heterocyclyl, saturated or unsaturated, unsubstituted or mono- or poly-substituted.

In another preferred embodiment of the invention, m represents 0, n represents 1 or 2 and $R^7$ represents $C_{1-8}$-alkyl or $C_{2-8}$-heteroalkyl, saturated or unsaturated; branched or unbranched, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{3-8}$-cycloalkyl or heterocyclyl, saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl.

In another preferred embodiment of the invention, m represents 0, n represents 1 or 2 and $R^7$ represents $C_{1-6}$-alkyl or $C_{2-6}$-heteroalkyl, saturated or unsaturated; branched or unbranched, unsubstituted or mono- or poly-substituted by one or more substituents selected independently of one another from the group consisting of F, Cl, $OCH_3$ and $CF_3$; $C_{3-8}$-cycloalkyl or heterocyclyl, saturated or unsaturated, unsubstituted or mono- or poly-substituted by one or more substituents selected independently of one another from the group consisting of F, Cl, $OCH_3$ and $CF_3$;

Preferably, $R^8$ is selected from the group consisting of $C_{1-10}$-alkyl or $C_{2-10}$-heteroalkyl, in each case saturated or unsaturated, branched or unbranched, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{3-10}$-cycloalkyl or heterocyclyl, in each case saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; aryl or heteroaryl, in each case unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{1-8}$-alkyl- or $C_{2-8}$-heteroalkyl-bridged $C_{3-10}$-cycloalkyl or heterocyclyl, in each case saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl, wherein the alkyl or heteroalkyl chain in each case can be branched or unbranched, saturated or unsaturated, unsubstituted; or $C_{1-8}$-alkyl- or $C_{2-8}$-heteroalkyl-bridged aryl or heteroaryl, in each case unsubstituted or mono- or poly-substituted by one or more substituents selected independently of one another from the group consisting of H; F; Cl; Br; I; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl, wherein the alkyl or heteroalkyl chain in each case can be branched or unbranched, saturated or unsaturated, unsubstituted;

Particularly preferably, $R^8$ is selected from the group consisting of $C_{1-8}$-alkyl or $C_{2-8}$-heteroalkyl, in each case saturated or unsaturated, branched or unbranched, unsubstituted or mono- or poly-substituted by one or more substituents selected independently of one another from the group consisting of F, Cl, Br, I, OH, =O, $OCF_3$, $SCF_3$, $CF_3$, $C_{1-4}$-alkyl and $OC_{1-4}$-alkyl; $C_{3-10}$-cycloalkyl or heterocyclyl, in each case saturated or unsaturated, unsubstituted or mono- or poly-substituted by one or more substituents selected independently of one another from the group consisting of F, Cl, Br, I, OH, =O, $OCF_3$, $SCF_3$, $CF_3$, $C_{1-4}$-alkyl and $OC_{1-4}$-alkyl; aryl or heteroaryl, in each case unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; aryl or heteroaryl, in each case unsubstituted or mono- or poly-substituted by one or more substituents selected independently of one another from the group consisting of H; F; Cl; Br; I; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{1-8}$-alkyl- or $C_{2-8}$-heteroalkyl-bridged $C_{3-10}$-cycloalkyl, saturated or unsaturated, unsubstituted or mono- or poly-substituted by one or more substituents selected independently of one another from the group consisting of F, Cl, Br, I, OH, =O, $OCF_3$, $SCF_3$, $CF_3$, $C_{1-8}$-alkyl and $OC_{1-8}$-alkyl, wherein the alkyl or heteroalkyl chain in each case can be branched or unbranched, saturated or unsaturated, unsubstituted; or $C_{1-8}$-alkyl- or $C_{2-8}$-heteroalkyl-bridged aryl or heteroaryl, in each case unsubstituted or mono- or poly-substituted by one or more substituents selected independently of one another from the group consisting of F, Cl, Br, I, OH, $NH_2$, $OCF_3$, $SCF_3$, $CF_3$, $C_{1-8}$-alkyl and $OC_{1-8}$-alkyl, wherein the alkyl or heteroalkyl chain in each case can be branched or unbranched, saturated or unsaturated, unsubstituted.

Most particularly preferably, $R^8$ is selected from the group consisting of methyl, ethyl, n-propyl, isopropyl, n-butyl, 2-butyl, tert-butyl, n-pentyl, isopentyl, neopentyl, n-hexyl, cyclopropyl, cyclobutyl, cyclopentyl, cyclohexyl, methyl-cyclopropyl, bethyl-cyclobutyl, methyl-cyclopentyl, methyl-cylohexyl, ethyl-cyclopropyl, ethyl-cyclobutyl, ethyl-cyclopentyl, ethyl-cyclohexyl, in each case unsubstituted or mono- or poly-substituted by one or more substituents selected from the group consisting of F, Cl, Br, I, $OCF_3$, $SCF_3$, $CF_3$, and $OC_{1-8}$-alkyl; or phenyl, benzyl or phenethyl, in each case unsubstituted or mono- or poly-substituted by one or more substituents selected from the group consisting of F, Cl, Br, I, $OCF_3$, $SCF_3$, $CF_3$, $C_{1-8}$-alkyl, $OC_{1-8}$-alkyl and CN.

Particular preference is given to compounds from the group 1 2-cyclohexyl-N-(2-(2-(phenylsulfonyl)ethylthio)quinolin-3-yl)acetamide;
2 N-(2-(2-(phenylsulfonyl)ethylthio)quinolin-3-yl)-2-(thiophen-2-yl)acetamide;
4 N-(2-(pentylthio)quinolin-3-yl)-2-(thiophen-2-yl)acetamide;

6 N-(2-(2-(phenylthio)ethylthio)quinolin-3-yl)-2-(thiophen-2-yl)acetamide;
7 N-(2-(ethylthio)quinolin-3-yl)-2-(thiophen-2-yl)acetamide;
9 N-(2-(ethylthio)quinolin-3-yl)-3,3-dimethylbutanamide;
11 N[2-ethylsulfanyl-7-(trifluoromethyl)-quinolin-3-yl]-3,3-dimethyl-butyramide
12 3-cyclopentyl-N-[2-ethylsulfanyl-7-(trifluoromethyl)-quinolin-3-yl]propionamide
14 2-(5-bicyclo[2.2.1]heptanyl)-N-(2-ethylsulfanyl-quinolin-3-yl)-acetamide
15 3-cyclopentyl-N-(2-ethylsulfanyl-quinolin-3-yl)-propionamide
16 2-(5-bicyclo[2.2.1]heptanyl)-N-[2-ethylsulfanyl-7-(trifluoromethyl)-quinolin-3-yl]-acetamide
17 3-cyclopentyl-N-[2-ethylsulfanyl-4-methyl-7-(trifluoromethyl)-quinolin-3-yl]-propionamide
18 N-[2-ethylsulfanyl-4-methyl-7-(trifluoromethyl)-quinolin-3-yl]-2-thiophen-2-yl-acetamide
or physiologically acceptable salts thereof.

The substituted 3-amino-2-mercaptoquinolines according to the invention and in each case the corresponding acids, bases, salts and solvates are suitable as pharmaceutical active ingredients in medicaments.

The invention therefore further provides a medicament comprising at least one substituted 3-amino-2-mercaptoquinoline of the general formula (1) according to the invention wherein the radicals $R^1$ to $R^8$ have the meaning given above and, optionally, one or more pharmaceutically acceptable auxiliary substances.

In addition to at least one compound according to the invention, the medicaments according to the invention optionally comprise suitable additives and/or auxiliary substances, that is to say also carriers, fillers, solvents, diluents, colourings and/or binders, and can be administered as liquid medicament forms in the form of injection solutions, drops or juices, as semi-solid medicament forms in the form of granules, tablets, pellets, patches, capsules, plasters/spray-on plasters or aerosols. The choice of auxiliary substances etc. and the amounts thereof to be used are dependent on whether the medicament is to be administered orally, perorally, parenterally, intravenously, intraperitoneally, intradermally, intramuscularly, intranasally, buccally, rectally or locally, for example to the skin, the mucosa or into the eyes. Preparations in the form of tablets, dragées, capsules, granules, drops, juices and syrups are suitable for oral administration, and solutions, suspensions, readily reconstitutable dry preparations and sprays are suitable for parenteral, topical and inhalatory administration. Compounds according to the invention in a depot, in dissolved form or in a plaster, optionally with the addition of agents that promote penetration through the skin, are suitable percutaneous forms of administration. Forms of preparation for administration orally or percutaneously can release the compounds according to the invention in a delayed manner. The compounds according to the invention can also be administered in parenteral long-term depot forms such as, for example, implants or implanted pumps. In principle, other further active ingredients known to the person skilled in the art can be added to the medicaments according to the invention.

The medicaments according to the invention are suitable for influencing KCNQ2/3 channels and exert an agonistic or antagonistic action, in particular an agonistic action.

The medicaments according to the invention are preferably suitable for the treatment of disorders or diseases that are mediated at least in part by KCNQ2/3 channels.

The medicaments according to the invention are suitable preferably for the treatment of one or more diseases selected from the group consisting of pain, especially pain selected from the group consisting of acute pain, chronic pain, neuropathic pain, muscular pain and inflammatory pain; epilepsy, urinary incontinence, anxiety, dependency, mania, bipolar disorders, migraine, cognitive diseases, dystonia-associated dyskinesias and/or urinary incontinence.

The medicaments according to the invention are suitable particularly preferably for the treatment of pain, most particularly preferably of chronic pain, neuropathic pain, inflammatory pain and muscular pain.

The medicaments according to the invention are also suitable particularly preferably for the treatment of epilepsy.

The invention further provides the use of at least one substituted 3-amino-2-mercaptoquinoline according to the invention, and optionally one or more pharmaceutically acceptable auxiliary substances, in the preparation of a medicament for the treatment of disorders or diseases that are mediated at least in part by KCNQ2/3 channels.

Preference is given to the use of at least one substituted 3-amino-2-mercaptoquinoline according to the invention, and optionally one or more pharmaceutically acceptable auxiliary substances, in the preparation of a medicament for the treatment of pain, especially pain selected from the group consisting of acute pain, chronic pain, neuropathic pain, muscular pain and inflammatory pain; epilepsy, urinary incontinence, anxiety, dependency, mania, bipolar disorders, migraine, cognitive diseases, dystonia-associated dyskinesias and/or urinary incontinence.

Particular preference is given to the use of at least one substituted 3-amino-2-mercaptoquinoline according to the invention, and optionally one or more pharmaceutically acceptable auxiliary substances, in the preparation of a medicament for the treatment of pain, most particularly preferably chronic pain, neuropathic pain, inflammatory pain and muscular pain.

Particular preference is given also to the use of at least one substituted 3-amino-2-mercaptoquinoline according to the invention, and optionally one or more pharmaceutically acceptable auxiliary substances, in the preparation of a medicament for the treatment of epilepsy.

The invention further provides at least one substituted 3-amino-2-mercaptoquinoline according to the invention, and optionally one or more pharmaceutically acceptable auxiliary substances, for the treatment of disorders or diseases that are mediated at least in part by KCNQ2/3 channels.

The invention further provides at least one substituted 3-amino-2-mercaptoquinoline according to the invention, and optionally one or more pharmaceutically acceptable auxiliary substances, for the treatment of pain, especially pain selected from the group consisting of acute pain, chronic pain, neuropathic pain, muscular pain and inflammatory pain; epilepsy, urinary incontinence, anxiety, dependency, mania, bipolar disorders, migraine, cognitive diseases, dystonia-associated dyskinesias and/or urinary incontinence.

Particular preference is given to at least one substituted 3-amino-2-mercaptoquinoline according to the invention, and optionally one or more pharmaceutically acceptable auxiliary substances, for the treatment of pain, most particularly preferably chronic pain, neuropathic pain, inflammatory pain and muscular pain.

Particular preference is given also to at least one substituted 3-amino-2-mercaptoquinoline according to the invention, and optionally one or more pharmaceutically acceptable auxiliary substances, for the treatment of epilepsy.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363). The effectiveness against epilepsy can be demonstrated, for example, in the DBA/2 mouse model (De Sarro et al., Naunyn-Schmiedeberg's Arch. Pharmacol. 2001, 363, 330-336).

The substituted 3-amino-2-mercaptoquinolines according to the invention preferably have an $EC_{50}$ value of not more than 10 µM or not more than 5 µM, more preferably not more than 3 µM or not more than 2 µM, yet more preferably not more than 1.5 µM or not more than 1 µM, most preferably not more than 0.8 µM or not more than 0.4 µM and especially not more than 0.3 µM or not more than 0.2 µM. Methods for determining the $EC_{50}$ value are known to the person skilled in the art. The $EC_{50}$ value is preferably determined by fluorimetry, particularly preferably as described under "Pharmacological Experiments".

The invention further provides processes for the preparation of the substituted 3-amino-2-mercaptoquinolines according to the invention.

The chemicals and reaction components used in the reactions described hereinbelow are available commercially or can in each case be prepared by conventional methods known to the person skilled in the art.

General Preparation Processes

Scheme 1:

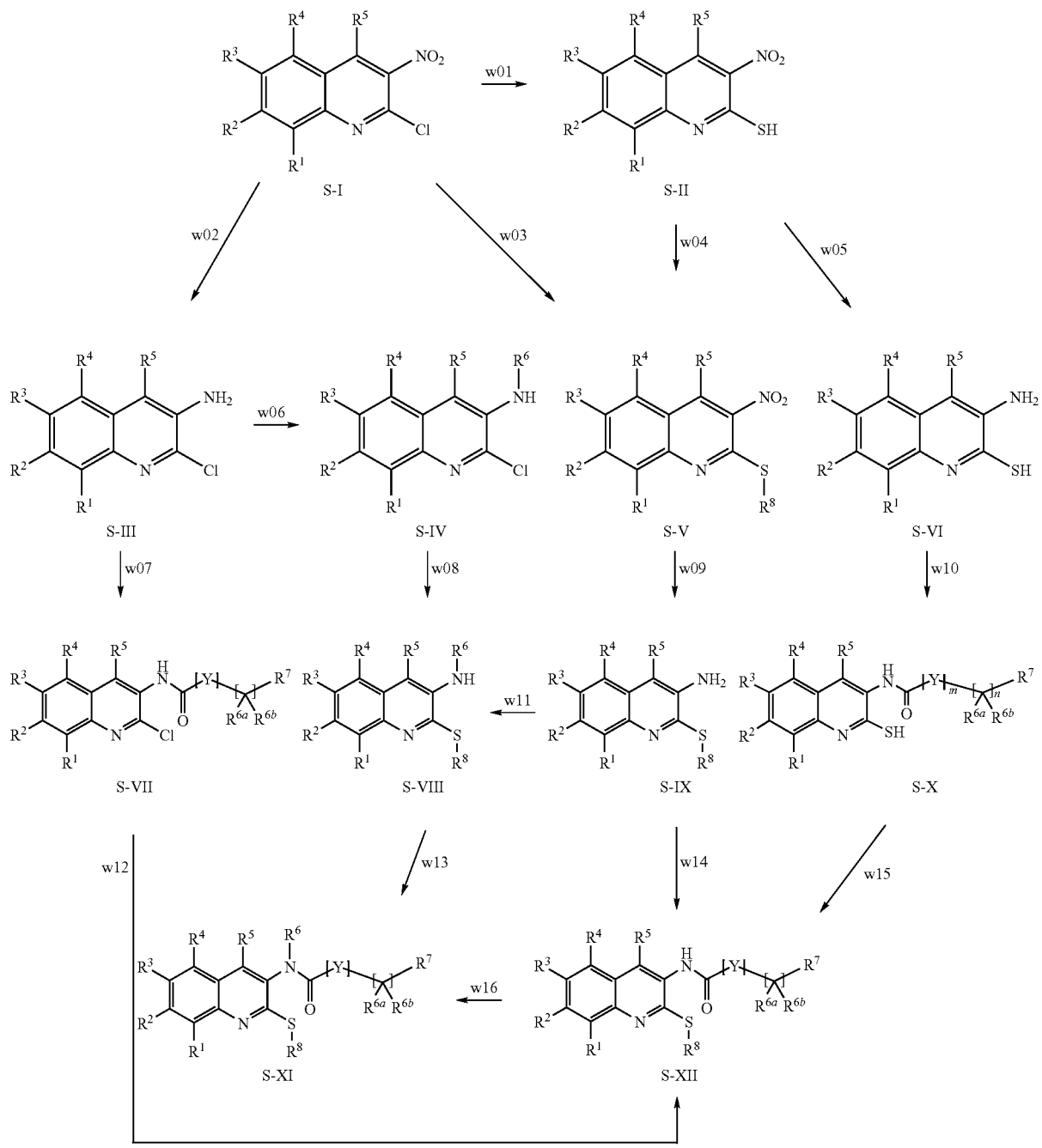

In step w01, the 2-halo-quinoline S-I, wherein X preferably represents F or chlorine, can first be converted by means of methods known to the person skilled in the art, for example by substitution with a thiol, for example 3-mercaptopropanoic acid ethyl ester, into the corresponding thioether, which can subsequently be cleaved, optionally in the presence of an acid or base, to give the thiol S-II.

In steps w02, w05 and w09, the nitro groups of compounds S-I, S-II and S-V can be converted into the corresponding amines S-III, S-VI and S-IX by means of reduction methods known to the person skilled in the art, for example in the presence of metals in acidic solution or by catalytic hydrogenation.

In steps w07, w10, w13 and w14, the amines S-III, S-VI, S-VIII and S-IX can be converted into the corresponding amides S-VII, S-IX, S-XI and S-XII. This can be achieved, for example, in each case by reaction with an acid chloride $R^7$—C(=O)—Cl by means of methods known to the person skilled in the art, optionally in the presence of a base, or by reaction with an acid $R^7$—C(=O)—OH in the presence of a suitable coupling reagent, for example HATU or CDI, optionally with the addition of a base.

In steps w04 and w15, the thiols S-II and S-X can be converted into the corresponding thioethers S-V and S-XII by means of methods known to the person skilled in the art. The thiols S-II and S-X can, for example, in each case be alkylated by the use of the alkyl halide $R^8$-Hal, optionally in the presence of a base.

In steps w03, w08 and w12, the thioethers S-V, S-VIII and S-XII can be formed starting from the 2-halo-quinolines S-I, S-IV and S-VII, wherein X in each case represents halogen, preferably fluorine or chlorine, by means of methods known to the person skilled in the art, for example in each case by alkylation with the corresponding thiol $R^8$—SH in an ipso substitution, optionally in the presence of a base.

In steps w06 and w11, the primary amines S-III, S-IX can be converted into the compounds S-IV and S-VIII by means of methods known to the person skilled in the art, for example reductive amination with the corresponding aldehydes or ketones with addition of a suitable reducing agent.

In step w16, the amide S-XII can be N-alkylated to give the compound S-XI by means of methods known to the person skilled in the art using suitable alkylating agents, optionally in the presence of a base.

The methods known to the person skilled in the art for carrying out reaction steps w01 to w16 are to be found in the standard works of organic chemistry, for example J. March, Advanced Organic Chemistry, Wiley & Sons, 6th edition, 2007; F. A. Carey, R. J. Sundberg, Advanced Organic Chemistry, Parts A and B, Springer, 5th edition, 2007); team of authors, Compendium of Organic Synthetic Methods, Wiley & Sons. Further methods and literature references can additionally be issued by customary databases such as the Reaxys® database of Elsevier, Amsterdam, NL or the SciFinder® database of the American Chemical Society, Washington, USA.

Description of the Exemplary Syntheses

| Abbreviations | |
|---|---|
| AcOH | acetic acid |
| aq. | aqueous |
| brine | sat. aq. NaCl soln. |
| BuLi | n-butyllithium |
| d | days |
| DCM | dichloromethane |
| DIPEA | N,N-diisopropylethylamine |
| DMF | N,N-dimethylformamide |
| EA | ethyl acetate |
| sat. | saturated |
| h | hour(s) |
| conc. | concentrated |
| soln. | solution |
| m/z | mass to charge ratio |
| M | molar |
| MeCN | acetonitrile |
| MeOH | methanol |
| min | minutes |
| MS | mass spectrometry |
| N/A | not available |
| $NEt_3$ | triethylamine |
| RG | retigabine |
| RT | room temperature 23 ± 7° C. |
| CC | column chromatography on silica gel |
| THF | tetrahydrofuran |
| vv | ratio by volume |

All starting materials not described explicitly were either available commerically (suppliers can be found, for example, in the Symyx® Available Chemicals database of MDL, San Ramon, US) or their synthesis has already been described exactly in the specialist literature (experimental procedures can be found, for example, in the Reaxys® database of Elsevier, Amsterdam, NL) or can be prepared by methods known to the person skilled in the art.

Silica gel 60 (0.040-0.063 mm) was used as the stationary phase for column chromatography (CC).

The analytical characterization of all intermediates and exemplary compounds was carried out by means of $^1$H-NMR spectroscopy. Investigations by mass spectrometry (MS, m/z indicated for $[M+H]^+$) were additionally carried out for all exemplary compounds and chosen intermediates.

Synthesis of Intermediates

Synthesis of Intermediate VA01: 2-(Phenylsulfonyl) ethanethiol a) Synthesis of S-2-(phenylsulfonyl)ethyl Ethanethiolate 3.6 ml (25.8 mmol) of $NEt_3$ and 3.5 ml (49.0 mmol) of thioacetic acid were added to a solution of 10.0 g (48.9 mmol) of (2-chloroethylsulfonyl)benzene in benzene (180 ml), and the mixture was then heated for 3 h at 80° C. The mixture was then diluted with EA and washed with water and brine. The organic phase was dried over $MgSO_4$, filtered and concentrated in vacuo. There were obtained as residue 11.6 g (47.5 mmol, 97%) of S-2-(phenylsulfonyl)-ethyl ethanethiolate, which was reacted further without additional purification.

b) Synthesis of 2-(phenylsulfonyl)ethanethiol

A solution of 11.6 g (47.5 mmol) of S-2-(phenylsulfonyl)-ethyl ethanethiolate in 10% methanolic hydrochloric acid was heated for 24 h at 80° C. Concentration in vacuo was then carried out. The residue was taken up in EA, and washing with water and brine was carried out. The organic phase was dried over $MgSO_4$, filtered and concentrated in vacuo. There were obtained as residue 9.0 g (44.5 mmol, 94%) of 2(phenylsulfonyl)ethanethiol, which was reacted further without additional purification.

Synthesis of Intermediate VB01: 3-Nitro-2-(2-(phenylsulfonyl)ethylthio)quinoline 1.76 g (8.7 mmol) of intermediate VA01 and 0.98 g (8.7 mmol) of potassium tert-butylate were added in succession to a solution of 1.21 g (5.8 mmol) of 2-chloro-3-nitroquinoline in THF (30 ml), and stirring was carried out for 16 h at RT. The reaction solution was then diluted with EA and washed with water and brine. The organic phase was dried over $Na_2SO_4$, filtered and concentrated in vacuo. Crystallization (DCM/hexane) yielded 539 mg (1.4 mmol, 25%) of 3-nitro-2-(2-(phenylsulfonyl)ethylthio)quinoline.

Synthesis of Intermediate VC01: 2-(2-(Phenylsulfonyl)ethylthio)quinolin-3-amine 290 mg (5.2 mmol) of iron powder were added to a solution of 700 mg (1.87 mmol) of intermediate VB01 in MeOH (10 ml), and the mixture was cooled to 0° C. 3.7 ml of conc. hydrochloric acid were then added dropwise, the temperature being maintained at 0-5° C. Heating was then carried out for 3 h at 70° C. and, after cooling the reaction solution to RT, filtration over kieselguhr was carried out. The filtrate was concentrated in vacuo and rendered basic with an aq. $NaHCO_3$ soln. The mixture was then extracted with EA and the organic phase was dried over $Na_2SO_4$, filtered and concentrated in vacuo. CC (EA/hexane 4:1) yielded 341 mg (0.99 mmol, 53%) of 2-(2-(phenylsulfonyl)ethylthio)quinolin-3-amine.

Synthesis of Intermediate VC05: 2-Chloro-7-(trifluoromethyl)quinolin-3-amine a) Synthesis of 2-chloro-7-(trifluoromethyl)quinoline-3-carboxylic Acid 11 ml of BuLi (1M in hexane) were added dropwise at −78° C. to a solution of 1.9 ml (11 mmol) of DIPEA in THF (77 ml). After stirring for 30 min at −78° C., a solution of 2.31 g (10 mmol) of 2-chloro-7-(trifluoromethyl)quinoline in THF (30 ml) was added and stirring was carried out for a further 30 min at −78° C. The reaction solution was then poured onto finely divided, solid $CO_2$. After heating to RT, most of the THF was removed in vacuo. A 1M aq. NaOH soln. was then added and the phases were separated. The aqueous phase was acidified with 10% hydrochloric acid and extracted with EA. The organic phase was washed with water and brine, dried over $Na_2SO_4$, filtered and concentrated in vacuo. There were obtained as residue 2.12 g (7.7 mmol, 71%) of 2-chloro-7-(trifluoromethyl)quinoline-3-carboxylic acid, which was reacted further without additional purification.

b) Synthesis of 2-chloro-7-(trifluoromethyl)quinolin-3-amine 20.6 g (75 mmol) of diphenyiphosphoryl azide were added at RT to a solution of 1.4 g (5 mmol) of 2-chloro-7-(trifluoromethyl)quinoline-3-carboxylic acid in benzene (500 ml), and the mixture was then heated for 5 h at 90° C. Concentration in vacuo was then carried out and the residue was taken up in THF (80 ml). 4N aq. LiOH soln. (30 ml) was added to this solution, and stirring was carried out for 1 h at RT. Dilution with water and extraction with EA were then carried out. The organic phase was washed with water and brine, dried over $Na_2SO_4$, filtered and concentrated in vacuo. CC (hexane/EA 9:1) of the residue yielded 310 mg (1.3 mmol, 26%) of 2-chloro-7-(trifluoromethyl)quinolin-3-amine.

Synthesis of Intermediate VC06: 2-(Ethylthio)-4-methyl-7-(trifluoromethyl)quinolin-3-amine a) Synthesis of 2-(2-chloro-4-methylquinolin-3-yl)isoindoline-1,3-dione 1.4 g (10.4 mmol) of $K_2CO_3$ were added to a solution of 2.7 g (6.9 mmol) of N-(2-acetylphenyl)-2-(1,3-dioxoisoindolin-2-yl)-acetamide in DMF (27 ml), and the mixture was heated for 16 h at 60° C. After cooling to RT, the pH was adjusted to 2-3 with 2N hydrochloric acid. The resulting precipitate was filtered off with suction and dried in vacuo at 70° C. 9 ml (97 mmol) of $POCl_3$ were added to the residue. This solution was heated for 2 h at 100° C. and then stirred for 16 h at RT. Toluene was then added and concentration was carried out in vacuo. This procedure was repeated, there being obtained as residue 2.13 g (5.5 mmol, 79%) of 2-(2-chloro-4-methylquinolin-3-yl)isoindoline-1,3-dione, which was reacted further without additional purification.

b) Synthesis of 2-(2-(ethylthio)-4-methylquinolin-3-yl)isoindoline-1,3-dione 2.1 g (15.4 mmol) of $K_2CO_3$ and 760 µl (10.3 mmol) of ethanethiol were added in succession to a solution of 2.1 g (5.1 mmol) of 2-(2-chloro-4-methylquinolin-3-yl)isoindoline-1,3-dione in DMF (36 ml). The mixture was then heated for 16 h at 60° C. A further 2.1 g (15.4 mmol) of $K_2CO_3$ and 760 µl (10.3 mmol) of ethanethiol were then added, and the mixture was again heated for 16 h at 50° C. After cooling to RT, the mixture was diluted with water and extracted twice with EA. The combined organic phases were washed with brine, dried over $MgSO_4$, filtered and concentrated in vacuo. There were obtained as residue 1.7 g (4.0 mmol, 78%) of 2-(2-(ethylthio)-4-methylquinolin-3-yl)isoindoline-1,3-dione, which was reacted further without additional purification.

c) Synthesis of 2-(ethylthio)-4-methyl-7-(trifluoromethyl)quinolin-3-amine

A solution of 1.67 g (4.0 mmol) of 2-(2-(ethylthio)-4-methylquinolin-3-yl)isoindoline-1,3-dione and 0.5 g (8.0 mmol) of hydrazine hydrate in EtOH (60 ml) was heated for 4 h at 70° C. and then stirred for 16 h at RT. The reaction solution was then extracted with EA (2×50 ml) and the combined organic phases were washed with brine, dried over $MgSO_4$, filtered and concentrated in vacuo. CC (hexane/EA 3:1) with the residue yielded 656 mg (2.3 mmol, 57%) of 2-(ethylthio)-4-methyl-7-(trifluoromethyl)quinolin-3-amine.

Synthesis of Further Intermediates

The synthesis of further intermediates was carried out according to the processes already described. Table 1 shows which compound was prepared by which process. It will be clear to the person skilled in the art which starting materials and reagents were used in each case.

TABLE 1

| Intermediate | Chemical name | Preparation analogous to intermediate | Yield [%] |
| --- | --- | --- | --- |
| VB02 | 3-nitro-2-(pentylthio)quinoline | VB01 | 75 |
| VC02 | 2-(pentylthio)quinolin-3-amine | VC01 | 78 |
| VC03 | 2-(2-(phenylthio)ethylthio)-quinolin-3-amine | VC01 | 63 |
| VC04 | 2-(ethylthio)quinolin-3-amine | VC01 | 55 |

Synthesis of the Exemplary Compounds

Synthesis of Exemplary Compound 3: 3-Cyclohexyl-N-(2-(2-(phenylsulfonyl)ethylthio)quinolin-3-yl)propanamide 255 µl (2.6 mmol) of DIPEA were added to a solution of 250 mg (0.73 mmol) of intermediate VC01 in DCM (4 ml), and the mixture was cooled to 0° C. 128 mg (0.73 mmol) of 3-cyclohexyl-propanoic acid chloride were then added. The reaction solution was then stirred for 16 h at RT, and then the mixture was diluted with DCM and washed with a sat. aq. $Na_2CO_3$ soln. and brine. The organic phase was dried over $Na_2SO_4$, filtered and concentrated in vacuo. CC (EA/hexane 4:1) yielded 162 mg (0.34 mmol, 46%) of 3-cyclohexyl-N-(2-(2-(phenylsulfonyl)ethylthio)quinolin-3-yl)propanamide. MS: m/z 483.2 $[M+H]^+$.

Synthesis of Exemplary Compound 10: N-[2-Ethylsulfanyl-7-(trifluoromethyl)quinolin-3-yl]-2-thiophen-2-yl-acetamide a) Synthesis of N-(2-chloro-7-(trifluoromethyl)quinolin-3-yl)-2-(thiophen-2-yl)acetamide 373 µl (4 mmol) of DIPEA and 385 mg (2.4 mmol) of 2-(thiophen-2-yl)acetyl chloride were added in succession at 0° C. to a solution of 493 mg (2 mmol) of 2-chloro-7-(trifluoromethyl)quinolin-3-amine (VC05) in DCM (14 ml). After stirring for 16 h at RT, the mixture was diluted with DCM. It was then washed with water and brine, dried over $Na_2SO_4$, filtered and concentrated in vacuo. CC (hexane/EA 19:1) of the residue yielded 321 mg (0.87 mmol, 44%) of N-(2-chloro-7-(trifluoromethyl)quinolin-3-yl)-2-(thiophen-2-yl)acetamide.

b) Synthesis of N-[2-ethylsulfanyl-7-(trifluoromethyl)-quinolin-3-yl]-2-thiophen-2-yl-acetamide 331 mg (2.4 mmol) of $K_2CO_3$ and 40 mg (1.6 mmol) of ethanethiol were added to a solution of 300 mg (0.81 mmol) of N-(2-chloro-7-(trifluoromethyl)quinolin-3-yl)-2-(thiophen-2-yl)acetamide in DMF (6 ml), and the mixture was heated for 16 h at 60° C. It was then diluted with water and extracted with EA. The organic phase was washed with water and brine, dried over $Na_2SO_4$, filtered and concentrated in vacuo. CC (hexane/EA 9:1) of the residue yielded 242 mg (0.6 mmol, 74%) of N-[2-ethylsulfanyl-7-(trifluoromethyl)-quinolin-3-yl]-2-thiophen-2-yl-acetamide. MS: m/z 397.1 $[M+H]^+$.

Synthesis of Exemplary Compound 13: 2-Cyclohexyl-N-(2-ethylsulfanyl-quinolin-3-yl)-acetamide 760 mg (6 mmol) of oxalyl chloride and a catalytic amount of DMF (100 µl) were added at 0° C. to a suspension of 427 mg (3 mmol) of 2-cyclohexylacetic acid in DCM (45 ml). After stirring for 4 h at RT, the mixture was concentrated in vacuo. The residue was taken up in dioxane (30 ml), and 670 mg (8 mmol) of $NaHCO_3$ were added. After stirring for 5 min at RT, 408 mg (2 mmol) of 2-(ethylthio)quinolin-3-amine (VC04) were added. After stirring for 16 h at RT, the reaction solution was diluted with EA and washed with a sat. aq. $NaHCO_3$ soln. and brine, dried over $Na_2SO_4$, filtered and concentrated in vacuo. CC (hexane/EA 19:1) of the residue yielded 397 mg (1.0 mmol, 51%) of 2-cyclohexyl-N-(2-ethylsulfanyl-quinolin-3-yl)-acetamide. MS: m/z 329.2 $[M+H]^+$.

Synthesis of Further Exemplary Compounds

The synthesis of further exemplary compounds was carried out according to the processes already described. Table 2 shows which compound was prepared by which process. It will be clear to the person skilled in the art which starting materials and reagents were used in each case.

TABLE 2

| Example | Chemical name | Preparation analogous to example | Yield [%] | MS m/z $[M + H]^+$ |
|---|---|---|---|---|
| 1 | 2-cyclohexyl-N-(2-(2-(phenylsulfonyl)-ethylthio)quinolin-3-yl)acetamide | 3 | 51 | 469.2 |
| 2 | N-(2-(2-(phenylsulfonyl)-ethylthio)quinolin-3-yl)-2-(thiophen-2-yl)acetamide | 3 | 73 | 469.1 |
| 4 | N-(2-(pentylthio)quinolin-3-yl)-2-(thiophen-2-yl)acetamide | 3 | 20 | 371.1 |
| 6 | N-(2-(2-(phenylthio)ethylthio)quinolin-3-yl)-2-(thiophen-2-yl)acetamide | 3 | 71 | 437.1 |
| 7 | N-(2-(ethylthio)quinolin-3-yl)-2-(thiophen-2-yl)acetamide | 3 | 60 | 329.1 |
| 9 | N-(2-(ethylthio)quinolin-3-yl)-3,3-dimethylbutanamide | 3 | 60 | 303.1 |
| 11 | N-[2-ethylsulfanyl-7-(trifluoromethyl)-quinolin-3-yl]-3,3-dimethyl-butyramide | 10 | 31 (over 2 stages) | 371.1 |
| 12 | 3-cyclopentyl-N-[2-ethylsulfanyl-7-(trifluoromethyl)-quinolin-3-yl]-propionamide | 10 | 38 (over 2 stages) | 397.1 |
| 14 | 2-(5-bicyclo[2.2.1]heptanyl)-N-(2-ethylsulfanyl-quinolin-3-yl)-acetamide | 13 | 28 | 341.2 |
| 15 | 3-cyclopentyl-N-(2-ethylsulfanyl-quinolin-3-yl)-propionamide | 13 | 56 | 329.2 |
| 16 | 2-(5-bicyclo[2.2.1]heptanyl)-N-[2-ethylsulfanyl-7-(trifluoromethyl)-quinolin-3-yl]-acetamide | 10 | 6 (over 2 stages) | 409.1 |
| 17 | 3-cyclopentyl-N-[2-ethylsulfanyl-4-methyl-7-(trifluoromethyl)-quinolin-3-yl]-propionamide | 3 | 18 | 411.2 |
| 18 | N-[2-ethylsulfanyl-4-methyl-7-(trifluoromethyl)-quinolin-3-yl]-2-thiophen-2-yl-acetamide | 3 | 24 | 411.1 |

Pharmacological Experiments

Fluorescence Assay using a Voltage Sensitive Dye

Human CHO—K1 cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% fetal calf serum (FCS) (Invitrogen, #10270-106, heat-inactivated) and the necessary selection antibiotics.

Before being sown out for the measurements, the cells are washed with a 1×DPBS buffer without $Ca^{2+}/Mg^{2+}$ (e.g. Invitrogen, #14190-094) and detached from the bottom of the culture vessel by means of Accutase (PAA Laboratories, #L11-007) (incubation with Accutase for 15 min at 37° C.). The cell count then present is determined using a CASY™ cell counter (TCC model, Schärfe System) in order subsequently to apply, depending on the density optimization for the individual cell line, 20,000-30,000 cells/well/100 µl of the described nutrient medium to 96-well measuring plates of the Corning™ CellBIND™ type (Flat Clear Bottom Black Polystyrene Microplates, #3340). Incubation is then carried out for one hour at room temperature, without gassing or adjusting the humidity, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, MDS Analytical Technologies™) is prepared by dissolving the contents of a vessel Membrane Potential Assay Kit Red Component A in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed with 200 µl of ES buffer, then covered with a layer of 100 µl of the dye solution prepared above and incubated for 45 min at room temperature with the exclusion of light.

The fluorescence measurements are carried out with a BMG Labtech FLUOstar™, BMG Labtech NOVOstar™ or BMG Labtech POLARstar™ instrument (525 nm excitation, 560 nm emission, Bottom Read mode). After incubation of the dye, 50 µl of the test substances in the desired concentrations, or 50 µl of ES buffer for control purposes, are introduced into separate cavities of the measuring plate and incubated for 30 min at room temperature while being shielded from light. The fluorescence intensity of the dye is then measured for 5 min and the fluorescence value $F_1$ of each well is thus determined at a given, constant time. 15 µl of a 100 mM KCl solution (final concentration 92 mM) are then added to each well. The change in fluorescence is subsequently measured until all the relevant measured values have been obtained (mainly 5-30 min). At a given time after KCl application, a fluorescence value $F_2$ is determined, in this case at the time of the fluorescence peak.

For calculation, the fluorescence intensity $F_2$ is compared with the fluorescence intensity $F_1$, and the agonistic activity of the target compound on the potassium channel is determined therefrom. $F_2$ and $F_1$ are calculated as follows:

$$\left(\frac{F_2 - F_1}{F_1}\right) \times 100 = \frac{\Delta F}{F}(\%)$$

In order to determine whether a substance has agonistic activity, $$\frac{\Delta F}{F},$$

for example, can be compared with $$\left(\frac{\Delta F}{F}\right)_K$$

of control cells.

$$\left(\frac{\Delta F}{F}\right)_K$$

is determined by adding to the reaction batch only the buffer solution instead of the test substance, determining the value $F_{1K}$ of the fluorescence intensity, adding the potassium ions as described above, and measuring a value $F_{2K}$ of the fluorescence intensity. $F_{2K}$ and $F_{1K}$ are then calculated as follows:

$$\left(\frac{F_{2K} - F_{1K}}{F_{1K}}\right) \times 100 = \left(\frac{\Delta F}{F}\right)_K (\%)$$

A substance has an agonistic activity on the potassium channel when $$\frac{\Delta F}{F}$$

is greater than $$\left(\frac{\Delta F}{F}\right)_K :$$

$$\frac{\Delta F}{F} > \left(\frac{\Delta F}{F}\right)_K$$

Independently of the comparison of $$\frac{\Delta F}{F} \text{ with } \left(\frac{\Delta F}{F}\right)_K$$

it is possible to conclude that a target compound has agonistic activity if an increase in $$\frac{\Delta F}{F}$$

is to be observed as the dosage of the target compound increases.

Calculations of $EC_{50}$ values are carried out with the aid of 'Prism v4.0' software (GraphPad Software™).

Formalin Test, Mouse

The formalin test (Dubuisson, D. and Dennis, S. G., 1977, Pain, 4, 161-174) represents a model for both acute and chronic pain. By means of a single formalin injection into the dorsal side of a rear paw, a biphasic nociceptive reaction is induced in freely mobile test animals; the reaction is detected by observing three behaviour patterns which are clearly distinguishable from one another. The reaction is two-phase: phase 1=immediate reaction (duration up to 10 min; shaking of the paw, licking), phase 2=late reaction (after a rest phase; likewise shaking of the paw, licking; duration up to 60 min). The 1st phase reflects a direct stimulation of the peripheral nocisensors with high spinal nociceptive input (acute pain phase); the 2nd phase reflects a spinal and peripheral hypersensitization (chronic pain phase). In the studies described here, the chronic pain component (phase 2) has been evaluated.

Formalin in a volume of 20 µl and a concentration of 1% is administered subcutaneously into the dorsal side of the right rear paw of each animal. The specific changes in behaviour, such as lifting, shaking or licking of the paw (score 3, Dubuisson & Dennis, 1977), are observed and recorded in the observation period of 21 to 24 minutes following the formalin injection. The behaviour of the animals after administration of the substance (n=10 per dose of substance) was compared with a control group which received vehicle (n=10).

On the basis of the quantification of the pain behaviour, the action of the substance in the formalin test was determined as the change in percent compared with the control. The $ED_{50}$ calculations ($ED_{50}$=mean effective dose) were carried out by means of regression analysis according to the method of Litchfield and Wilcoxon (Litchfield, J. T., Wilcoxon, J. J., 1949, J. Pharmacol. Exp. Ther. 96, 99—113). The time of administration of the compound before the formalin injection was chosen as 5 min in the case of intravenous administration and 30 min in the case of oral administration.

Pharmacological Data

The results from the pharmacological models described above are summarized in Table 3.

TABLE 3

| Ex. No. | Fluorimetry EC50 [nM] | Fluorimetry % efficacy (retigabine = 100%) | Formalin Test mouse IV effect @ dose [mg/kg] |
|---|---|---|---|
| 1 | 253 | 80 | |
| 2 | 67 | 80 | |
| 3 | 174 | 97 | |
| 4 | 107 | 60 | |
| 6 | | 25 | |
| 7 | 156 | 93 | 24% @ 1 |
| 9 | 414 | 142 | |
| 10 | 1153 | 57 | |
| 11 | | 35 | |
| 12 | 5024 | 62 | |
| 13 | 150 | 101 | |
| 14 | 204 | 179 | |
| 15 | 82 | 143 | 17% @ 1 |
| 16 | 647 | 66 | |
| 17 | 66 | 107 | 90% @ 0.68 |
| 18 | 94 | 140 | 43% @ 1 |

The invention claimed is:
1. A substituted 3-amino-2-mercaptoquinoline of the formula:

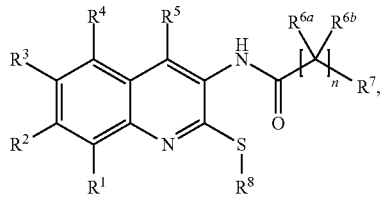

wherein
n represents an integer from 1, 2 or 3,
$R^1$, $R^2$, $R^3$ and $R^4$ each independently of the others are selected from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl, in each case saturated or unsaturated, branched or unbranched, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{3-6}$-cycloalkyl or heterocyclyl, in each case saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl;

$R^5$ is selected from the group consisting of H; F; Cl; Br; I; $NO_2$; $CF_3$; CN; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl, in each case saturated or unsaturated, branched or unbranched, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{3-6}$-cycloalkyl or heterocyclyl, in each case saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl;

$R^{6a}$ and $R^{6b}$ each independently of the other represents H; F; Cl; Br; I; methyl; ethyl; n-propyl; isopropyl; n-butyl; sec-butyl; tert-butyl; OH; O-methyl or O-ethyl;

$R^7$ denotes $C_{1-8}$-alkyl or $C_{2-8}$-heteroalkyl, saturated or unsaturated; branched or unbranched, unsubstituted or mono- or poly-substituted by one ore more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{3-8}$-cycloalkyl or heterocyclyl, saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; aryl or heteroaryl, in each case unsubstituted or mono- or poly-substituted by one or more substituents selected independently of one another from the group consisting of H; F; Cl; Br; I; $NO_2$; $CF_3$; CN; $NO_2$; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl;

with the proviso that, when $R^7$ denotes heterocyclyl, the heterocyclyl can be bound via a carbon atom of the heterocyclyl, and $R^8$ is selected from the group consisting of $C_{1-10}$-alkyl or $C_{2-10}$-heteroalkyl, in each case saturated or unsaturated, branched or unbranched, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{3-10}$-cycloalkyl or heterocyclyl, in each case saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; aryl or heteroaryl, in each case unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl; $C_{1-8}$-alkyl- or $C_{2-8}$-heteroalkyl-bridged $C_{3-10}$-cycloalkyl or heterocyclyl, in each case saturated or unsaturated, unsubstituted or mono- or poly-substituted by one or more substituents selected independently of one another from the group consisting of H; F; Cl; Br; I; $NO_2$; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl, wherein the alkyl or heteroalkyl chain in each case can be branched or unbranched, saturated or unsaturated, unsubstituted; or $C_{1-8}$-alkyl- or $C_{2-8}$-heteroalkyl-bridged aryl or heteroaryl, in each case unsubstituted or mono- or poly-substituted by one or more substituents selected independently of one another from the group consisting of H; F; Cl; Br; I; $CF_3$; CN; OH; $OCF_3$; SH; $SCF_3$; $NH_2$; $C_{1-6}$-alkyl, O—$C_{1-6}$-alkyl, O—C(=O)—$C_{1-6}$-alkyl, S—$C_{1-6}$-alkyl, NH($C_{1-6}$-alkyl), N($C_{1-6}$-alkyl)$_2$, NH—C(=O)—$C_{1-6}$-alkyl, N(C(=O)—$C_{1-6}$-alkyl)$_2$ or C(=O)—$C_{1-6}$-alkyl, wherein the alkyl or heteroalkyl chain in each case can be branched or unbranched, saturated or unsaturated, unsubstituted;

said substituted 3-amino-2-mercaptoquinoline being in the form of a free compound or a salt of physiologically acceptable acids or bases.

2. The mercaptoquinoline according to claim 1, wherein $R^7$ denotes heterocyclyl, the heterocyclyl being bound via a carbon atom of the heterocyclyl.

3. The mercaptoquinoline according to claim 1, wherein $R^1$, $R^2$, $R^3$ and $R^4$ each independently of the others represents H; F; Cl; CN; $OCF_3$; $SCF_3$; $CF_3$; $CH_3$ or $OCH_3$; and $R^5$ denotes H, F, Cl, $OCF_3$, $SCF_3$, $C_{1-6}$-alkyl, O—$C_{1-6}$-alkyl, or S—$C_{1-6}$-alkyl.

4. The mercaptoquinoline according claim 1, wherein $R^7$ represents $C_{2-6}$-alkyl or $C_{2-6}$-heteroalkyl, saturated or unsaturated, branched or unbranched, unsubstituted; $C_{3-8}$-cycloalkyl or heterocyclyl, saturated or unsaturated, unsubstituted; phenyl, furyl, thienyl or pyridyl, in each case unsubstituted or mono- or poly-substituted by one or more substituents selected independently of one another from the group consisting of F, Cl, Br, I, CN; $CF_3$, $OCF_3$, $SCF_3$, $CH_3$ and $OCH_3$.

5. The mercaptoquinoline according to claim 1, wherein n represents 1 and $R^7$ represents aryl or heteroaryl, in each case unsubstituted or mono- or poly-substituted.

6. The mercaptoquinoline according to claim 1, selected from the group consisting of:
1. 2-cyclohexyl-N-(2-(2-(phenylsulfonyl)ethylthio)quinolin-3-yl)acetamide;
2. N-(2-(2-(phenylsulfonyl)ethylthio)quinolin-3-yl)-2-(thiophen-2-yl)acetamide;
3. 3-cyclohexyl-N-(2-(2-(phenylsulfonyl)-ethylthio)quinolin-3-yl)propanamide;
4. N-(2-(pentylthio)quinolin-3-yl)-2-(thiophen-2-yl)acetamide;
6. N-(2-(2-(phenylthio)ethylthio)quinolin-3-yl)-2-(thiophen-2-yl)acetamide;
7. N-(2-(ethylthio)quinolin-3-yl)-2-(thiophen-2-yl)acetamide;
9. N-(2-(ethylthio)quinolin-3-yl)-3,3-dimethylbutanamide;
10. N-[2-ethylsulfanyl-7-(trifluoromethyl)-quinolin-3-yl]-2-thiophen-2-yl-acetamide;
11. N[2-ethylsulfanyl-7-(trifluoromethyl)-quinolin-3-yl]-3,3-dimethyl-butyramide
12. 3-cyclopentyl-N-[2-ethylsulfanyl-7-(trifluoromethyl)-quinolin-3-yl]propionamide
13. 2-cyclohexyl-N-(2-ethylsulfanyl-quinolin-3-yl)-acetamide;
14. 2-(5-bicyclo[2.2.1]heptanyl)-N-(2-ethylsulfanyl-quinolin-3-yl)-acetamide
15. 3-cyclopentyl-N-(2-ethylsulfanyl-quinolin-3-yl)-propionamide
16. 2-(5-bicyclo[2.2.1]heptanyl)-N-[2-ethylsulfanyl-7-(trifluoromethyl)-quinolin-3-yl]-acetamide
17. 3-cyclopentyl-N-[2-ethylsulfanyl-4-methyl-7-(trifluoromethyl)-quinolin-3-yl]-propionamide
18. N-[2-ethylsulfanyl-4-methyl-7-(trifluoromethyl)-quinolin-3-yl]-2-thiophen-2-yl-acetamide, and the physiologically acceptable salts thereof.

7. A pharmaceutical composition comprising at least one 3-amino-2-mercaptoquinoline according to claim 1, in the form of an individual stereoisomer or a mixture thereof, in the form of a free compound and/or a physiologically acceptable salt thereof, and optionally one or more suitable additives and/or auxiliary substances and/or optionally further active ingredients.

* * * * *

UNITED STATES PATENT AND TRADEMARK OFFICE
CERTIFICATE OF CORRECTION

PATENT NO. : 8,207,342 B2  
APPLICATION NO. : 12/720770  
DATED : June 26, 2012  
INVENTOR(S) : Kühnert et al.

Page 1 of 1

It is certified that error appears in the above-identified patent and that said Letters Patent is hereby corrected as shown below:

In the Specification

Column 5, line 1, "-heteroalkyl or C" -- should read -- -heteroalkyl or C --.

Column 7, lines 47-48, "-C≡O-CH$_2$-CH$_2$-" -- should read -- -C≡C-CH$_2$-CH$_2$- --.

Column 12, line 28, "ore" -- should read -- or --.

Column 12, line 38, "C$_{1-6}$-alkyl, O-C" -- should read -- C$_{1-6}$-alkyl, O-C$_{1-6}$-alkyl, O-C --.

Column 13, line 63, "O-C$_{1-6}$-alkyl, S-C$_{1-6}$-alkyl" -- should read -- O-C$_{1-6}$-alkyl, O-C(=O)-C$_{1-6}$-alkyl, S-C$_{1-6}$-alkyl --.

Column 20, line 41, "Ethanethiolate" -- should read -- ethanethiolate --.

Column 21, line 20, "VCO5" -- should read -- VC05 --.

Column 21, line 23, "Acid" -- should read -- acid --.

Column 21, line 41, "diphenyiphosphoryl" -- should read -- diphenylphosphoryl --.

In the Claims

Column 28, line 42, "one ore more" -- should read -- one or more --.

Signed and Sealed this  
Eleventh Day of February, 2014

Michelle K. Lee  
*Deputy Director of the United States Patent and Trademark Office*